(12) United States Patent
Timberlake et al.

(10) Patent No.: US 8,317,726 B2
(45) Date of Patent: Nov. 27, 2012

(54) BIOPSY FORCEPS ASSEMBLIES

(75) Inventors: Tyler Timberlake, Wolfeboro, NH (US);
Changqing Li, Northborough, MA (US);
Otto Anderhub, Miami, FL (US);
Douglas M. Bontrager, Miami, FL (US); Gerardo Martin, Hialeah, FL (US); Robert B. DeVries, Northborough, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 179 days.

(21) Appl. No.: 12/816,248

(22) Filed: Jun. 15, 2010

(65) Prior Publication Data

US 2010/0318119 A1 Dec. 16, 2010

Related U.S. Application Data

(63) Continuation of application No. 11/128,319, filed on May 13, 2005, now Pat. No. 7,762,960.

(51) Int. Cl.
*A61B 17/28* (2006.01)

(52) U.S. Cl. ........................................... 600/564

(58) Field of Classification Search .................. 606/168, 606/169, 174, 180; 600/562–568
See application file for complete search history.

(56) References Cited

U.S. PATENT DOCUMENTS

| | | | |
|---|---|---|---|
| 30,471 A | 10/1860 | Dudley | |
| 1,609,014 A | 11/1926 | Dowd | |
| 1,615,494 A | 1/1927 | Waring | |
| 1,931,740 A | 7/1932 | Ryan | |
| 1,924,348 A | 8/1933 | Brown | |
| 2,115,298 A | 4/1937 | Brown | |
| 2,131,780 A | 10/1938 | Storz | |
| 2,258,287 A | 10/1941 | Grieshaber | |
| 2,729,210 A | 1/1956 | Spencer | |
| 2,751,908 A | 6/1956 | Wallace | |
| 2,778,357 A | 1/1957 | Leibinger et al. | |
| 2,845,072 A * | 7/1958 | Shafer | 606/169 |
| 3,503,397 A | 3/1970 | Raible et al. | |
| 3,590,808 A | 7/1971 | Muller | |
| 3,608,554 A | 9/1971 | McGuinness et al. | |
| 3,683,892 A | 8/1972 | Harris | |
| 3,840,003 A | 10/1974 | Komiya | |
| 3,844,272 A | 10/1974 | Banko | |
| 3,895,636 A | 7/1975 | Schmidt | |
| 4,038,987 A | 8/1977 | Komiya | |

(Continued)

FOREIGN PATENT DOCUMENTS

DE  34 18 103  11/1985

(Continued)

OTHER PUBLICATIONS

International Search Report from PCT/US2006/018263 (2 pages), Feb. 10, 2006.

(Continued)

*Primary Examiner* — Max Hindenburg
*Assistant Examiner* — Michael C Stout
(74) *Attorney, Agent, or Firm* — Bookoff McAndrews, PLLC

(57) ABSTRACT

Embodiments of the invention include devices for obtaining tissue including a proximal actuator and a distal assembly having first and second end effectors. The first and second end effectors include the features of at least one element within the inner surface either of the first and second end effectors for aiding in the capture and retention of a targeted tissue sample.

20 Claims, 13 Drawing Sheets

U.S. PATENT DOCUMENTS

| | | | |
|---|---|---|---|
| 4,522,206 A | 6/1985 | Whipple et al. | |
| 4,598,710 A | 7/1986 | Kleinberg et al. | |
| 4,605,002 A | 8/1986 | Rebuffat | |
| 4,632,110 A | 12/1986 | Sanagi | |
| 4,644,951 A | 2/1987 | Bays | |
| 4,651,752 A | 3/1987 | Fuerst | |
| 4,651,753 A | 3/1987 | Lifton | |
| 4,656,999 A | 4/1987 | Storz | |
| 4,662,371 A | 5/1987 | Whipple et al. | |
| 4,669,471 A | 6/1987 | Hayashi | |
| 4,721,116 A | 1/1988 | Schintgen et al. | |
| 4,763,668 A | 8/1988 | Macek et al. | |
| 4,785,825 A * | 11/1988 | Romaniuk et al. | 600/564 |
| 4,815,476 A | 3/1989 | Clossick | |
| 4,817,630 A | 4/1989 | Schintgen et al. | |
| 4,887,612 A | 12/1989 | Esser et al. | |
| 4,896,678 A | 1/1990 | Ogawa | |
| 4,907,599 A | 3/1990 | Taylor | |
| 4,909,789 A | 3/1990 | Taguchi et al. | |
| 4,936,312 A | 6/1990 | Tsukagoshi | |
| 4,953,559 A | 9/1990 | Salerno | |
| 4,955,897 A | 9/1990 | Ship | |
| 4,971,067 A | 11/1990 | Boldud et al. | |
| 4,982,727 A | 1/1991 | Sato | |
| 4,986,279 A | 1/1991 | O'Neill | |
| 4,986,825 A | 1/1991 | Bays et al. | |
| 4,994,024 A | 2/1991 | Falk | |
| 5,052,402 A | 10/1991 | Bencini et al. | |
| 5,059,214 A | 10/1991 | Akopov et al. | |
| 5,082,000 A | 1/1992 | Picha et al. | |
| 5,100,430 A | 3/1992 | Avellanet et al. | |
| 5,125,779 A | 6/1992 | Hallock et al. | |
| 5,133,727 A | 7/1992 | Bales et al. | |
| 5,147,371 A | 9/1992 | Washington et al. | |
| 5,148,813 A | 9/1992 | Bucalo | |
| 5,161,542 A | 11/1992 | Palestrant | |
| 5,170,800 A | 12/1992 | Smith et al. | |
| 5,172,700 A | 12/1992 | Bencini et al. | |
| 5,176,687 A | 1/1993 | Hasson et al. | |
| 5,183,052 A | 2/1993 | Terwilliger | |
| 5,183,054 A | 2/1993 | Burkholder et al. | |
| 5,188,118 A | 2/1993 | Terwilliger | |
| 5,190,555 A | 3/1993 | Wetter et al. | |
| 5,192,286 A | 3/1993 | Phan et al. | |
| 5,195,533 A | 3/1993 | Chin et al. | |
| 5,197,968 A | 3/1993 | Clement | |
| 5,217,458 A | 6/1993 | Parins | |
| 5,238,002 A | 8/1993 | Delvin et al. | |
| 5,249,582 A | 10/1993 | Taylor | |
| 5,258,004 A | 11/1993 | Bales et al. | |
| 5,261,918 A | 11/1993 | Phillips et al. | |
| 5,263,967 A | 11/1993 | Lyons, III et al. | |
| 5,267,641 A | 12/1993 | Hallstrom, Jr. | |
| 5,285,795 A | 2/1994 | Ryan et al. | |
| 5,288,451 A | 2/1994 | Schad | |
| 5,295,990 A | 3/1994 | Levin | |
| 5,300,087 A | 4/1994 | Knoepfler | |
| 5,304,203 A | 4/1994 | El-Mallawany et al. | |
| 5,304,471 A | 4/1994 | El-Mallawany et al. | |
| 5,316,013 A | 5/1994 | Striebel, II et al. | |
| 5,318,528 A * | 6/1994 | Heaven et al. | 604/95.01 |
| 5,330,502 A | 7/1994 | Hassler et al. | |
| 5,341,815 A | 8/1994 | Cofone et al. | |
| 5,342,389 A | 8/1994 | Haber et al. | |
| 5,348,023 A | 9/1994 | McLucas | |
| 5,352,184 A | 10/1994 | Goldberg et al. | |
| 5,354,303 A | 10/1994 | Spaeth et al. | |
| 5,354,311 A | 10/1994 | Kambin et al. | |
| 5,366,467 A | 11/1994 | Lynch et al. | |
| 5,368,597 A | 11/1994 | Pagedas | |
| 5,370,659 A | 12/1994 | Sakashita | |
| 5,372,124 A | 12/1994 | Takayama et al. | |
| 5,373,854 A | 12/1994 | Kolozsi | |
| 5,374,277 A | 12/1994 | Hassler | |
| 5,383,471 A * | 1/1995 | Funnell | 600/564 |
| 5,383,888 A | 1/1995 | Zvenyatsky et al. | |
| 5,385,570 A | 1/1995 | Gordon | |
| 5,394,885 A | 3/1995 | Francese | |
| 5,396,900 A * | 3/1995 | Slater et al. | 600/564 |
| 5,419,220 A | 5/1995 | Cox | |
| 5,419,339 A | 5/1995 | Palmer | |
| 5,423,854 A | 6/1995 | Martin et al. | |
| 5,439,478 A | 8/1995 | Palmer | |
| 5,443,463 A * | 8/1995 | Stern et al. | 606/51 |
| 5,449,001 A | 9/1995 | Terwilliger | |
| 5,454,378 A | 10/1995 | Palmer et al. | |
| 5,462,546 A | 10/1995 | Rydell | |
| 5,465,731 A | 11/1995 | Bell et al. | |
| 5,471,992 A * | 12/1995 | Banik et al. | 600/564 |
| 5,476,099 A | 12/1995 | Robinson et al. | |
| 5,482,054 A * | 1/1996 | Slater et al. | 600/564 |
| 5,496,347 A | 3/1996 | Hashiguchi et al. | |
| 5,507,296 A * | 4/1996 | Bales et al. | 600/564 |
| 5,511,556 A | 4/1996 | DeSantis | |
| 5,535,754 A | 7/1996 | Doherty | |
| 5,538,008 A * | 7/1996 | Crowe | 600/564 |
| 5,542,432 A | 8/1996 | Slater et al. | |
| 5,553,624 A | 9/1996 | Francese et al. | |
| 5,558,100 A | 9/1996 | Cox | |
| 5,560,373 A | 10/1996 | DeSantis | |
| 5,562,102 A | 10/1996 | Taylor | |
| 5,564,436 A | 10/1996 | Hakky et al. | |
| 5,569,299 A | 10/1996 | Dill et al. | |
| 5,571,129 A | 11/1996 | Porter | |
| 5,573,008 A | 11/1996 | Robinson et al. | |
| 5,591,202 A | 1/1997 | Slater et al. | |
| 5,595,185 A | 1/1997 | Erlich | |
| 5,601,585 A | 2/1997 | Banik et al. | |
| 5,601,599 A | 2/1997 | Nunez | |
| 5,603,711 A | 2/1997 | Parins et al. | |
| 5,613,499 A | 3/1997 | Palmer et al. | |
| 5,636,639 A | 6/1997 | Turturro et al. | |
| 5,638,827 A | 6/1997 | Palmer et al. | |
| 5,643,307 A | 7/1997 | Turkel et al. | |
| 5,645,075 A * | 7/1997 | Palmer et al. | 600/562 |
| 5,647,115 A | 7/1997 | Tovey et al. | |
| 5,647,372 A | 7/1997 | Tovey et al. | |
| 5,653,713 A | 8/1997 | Michelson | |
| 5,665,050 A | 9/1997 | Benecke | |
| 5,666,965 A | 9/1997 | Bales et al. | |
| 5,667,525 A | 9/1997 | Ishibashi | |
| 5,669,394 A | 9/1997 | Bergey et al. | |
| 5,674,220 A | 10/1997 | Fox et al. | |
| 5,681,324 A | 10/1997 | Kammerer et al. | |
| 5,681,348 A | 10/1997 | Sato | |
| 5,683,359 A | 11/1997 | Farkas et al. | |
| 5,683,388 A * | 11/1997 | Slater | 606/51 |
| 5,683,413 A | 11/1997 | Miyagi | |
| 5,695,521 A | 12/1997 | Anderhub | |
| 5,695,522 A | 12/1997 | LeMaire, III et al. | |
| 5,697,949 A | 12/1997 | Anderhub | |
| 5,700,276 A | 12/1997 | Benecke | |
| 5,706,824 A | 1/1998 | Whittier | |
| 5,707,392 A | 1/1998 | Kortenbach | |
| 5,716,374 A | 2/1998 | Francese et al. | |
| 5,720,754 A | 2/1998 | Middleman et al. | |
| 5,722,421 A | 3/1998 | Francese et al. | |
| 5,735,289 A | 4/1998 | Pfeffer et al. | |
| 5,741,285 A | 4/1998 | McBrayer et al. | |
| 5,743,906 A | 4/1998 | Parins et al. | |
| 5,746,216 A | 5/1998 | Turturro et al. | |
| 5,746,740 A | 5/1998 | Nicholas | |
| 5,759,187 A | 6/1998 | Nakao et al. | |
| 5,762,069 A | 6/1998 | Kelleher et al. | |
| 5,762,070 A * | 6/1998 | Nagamatsu | 600/564 |
| 5,762,613 A | 6/1998 | Sutton | |
| 5,766,177 A | 6/1998 | Lucas-Dean et al. | |
| 5,766,184 A | 6/1998 | Matsuno et al. | |
| 5,775,333 A | 7/1998 | Burbank et al. | |
| 5,776,075 A | 7/1998 | Palmer | |
| 5,779,646 A | 7/1998 | Koblish et al. | |
| 5,779,648 A | 7/1998 | Banik et al. | |
| 5,779,686 A | 7/1998 | Sato et al. | |
| 5,779,716 A | 7/1998 | Cano et al. | |
| 5,795,308 A | 8/1998 | Russin | |
| 5,807,275 A | 9/1998 | Russin | |
| 5,807,277 A | 9/1998 | Swaim | |

| | | | | | | |
|---|---|---|---|---|---|---|
| 5,810,744 A | 9/1998 | Chu et al. | | 6,155,988 A | 12/2000 | Peters |
| 5,810,876 A | 9/1998 | Kelleher | | 6,159,162 A * | 12/2000 | Kostylev et al. ............ 600/564 |
| 5,819,738 A | 10/1998 | Slater | | 6,168,603 B1 | 1/2001 | Leslie et al. |
| 5,820,630 A | 10/1998 | Lind | | 6,171,315 B1 | 1/2001 | Chu et al. |
| 5,823,971 A | 10/1998 | Robinson et al. | | 6,174,292 B1 | 1/2001 | Kortenbach et al. |
| 5,827,299 A * | 10/1998 | Thomason et al. ............ 606/148 | | 6,174,318 B1 | 1/2001 | Bates et al. |
| 5,840,043 A | 11/1998 | Palmer et al. | | 6,183,482 B1 | 2/2001 | Bates et al. |
| 5,840,044 A | 11/1998 | Dassa et al. | | 6,190,399 B1 | 2/2001 | Palmer et al. |
| 5,843,000 A | 12/1998 | Nishioka et al. | | 6,193,671 B1 * | 2/2001 | Turturro et al. ............ 600/564 |
| 5,846,248 A | 12/1998 | Chu et al. | | 6,193,737 B1 | 2/2001 | Ouchi |
| 5,848,978 A | 12/1998 | Cecchi | | 6,206,904 B1 | 3/2001 | Ouchi |
| 5,849,022 A | 12/1998 | Sakashita et al. | | 6,217,587 B1 | 4/2001 | Tsuruta |
| 5,853,374 A | 12/1998 | Hart et al. | | 6,224,612 B1 | 5/2001 | Bates |
| 5,865,724 A | 2/1999 | Palmer et al. | | 6,228,095 B1 | 5/2001 | Dennis |
| 5,871,453 A | 2/1999 | Banik et al. | | 6,231,522 B1 | 5/2001 | Voegele et al. |
| 5,893,876 A | 4/1999 | Turkel et al. | | 6,241,687 B1 | 6/2001 | Voegele et al. |
| 5,895,361 A | 4/1999 | Turturro | | 6,248,081 B1 | 6/2001 | Nishtalas et al. |
| 5,897,507 A | 4/1999 | Kortenbach et al. | | 6,258,102 B1 | 7/2001 | Pagedas |
| 5,899,914 A | 5/1999 | Zirps et al. | | 6,261,242 B1 | 7/2001 | Roberts et al. |
| 5,906,630 A | 5/1999 | Anderhub | | 6,264,617 B1 | 7/2001 | Bales et al. |
| 5,908,381 A | 6/1999 | Aznoian et al. | | 6,264,618 B1 | 7/2001 | Landi et al. |
| 5,908,437 A | 6/1999 | Asano et al. | | 6,264,663 B1 | 7/2001 | Cano |
| 5,919,206 A | 7/1999 | Gengler et al. | | 6,273,860 B1 | 8/2001 | Kastyler et al. |
| 5,921,915 A | 7/1999 | Aznoian et al. | | 6,273,861 B1 | 8/2001 | Bates et al. |
| 5,922,002 A | 7/1999 | Yoon | | 6,273,887 B1 * | 8/2001 | Yamauchi et al. ............ 606/48 |
| 5,928,161 A | 7/1999 | Krulevitch et al. | | 6,280,398 B1 | 8/2001 | Ritchart et al. |
| 5,928,163 A * | 7/1999 | Roberts et al. ............ 600/567 | | 6,280,451 B1 | 8/2001 | Bates et al. |
| 5,928,164 A | 7/1999 | Burbank et al. | | 6,280,458 B1 | 8/2001 | Boche et al. |
| 5,944,673 A | 8/1999 | Gregoire et al. | | 6,283,924 B1 | 9/2001 | Ouchi |
| 5,947,996 A * | 9/1999 | Logeman ............ 606/205 | | 6,299,630 B1 | 10/2001 | Yamamoto |
| 5,951,488 A | 9/1999 | Slater et al. | | 6,309,404 B1 * | 10/2001 | Krzyzanowski ............ 606/208 |
| 5,957,863 A | 9/1999 | Koblish et al. | | 6,315,780 B1 | 11/2001 | Lalonde |
| 5,957,932 A | 9/1999 | Bates et al. | | 6,322,522 B1 | 11/2001 | Zimmon |
| 5,961,534 A | 10/1999 | Banik et al. | | 6,328,701 B1 | 12/2001 | Terwilliger |
| 5,964,716 A | 10/1999 | Gregoire et al. | | 6,331,165 B1 | 12/2001 | Turturro et al. |
| 5,967,997 A | 10/1999 | Turturro et al. | | 6,350,266 B1 | 2/2002 | White et al. |
| 5,971,940 A | 10/1999 | Baker et al. | | 6,364,846 B1 | 4/2002 | Nakamura |
| 5,976,130 A | 11/1999 | McBrayer et al. | | 6,368,290 B1 | 4/2002 | Baska |
| 5,980,468 A | 11/1999 | Zimmon | | 6,375,661 B1 | 4/2002 | Chu et al. |
| 6,007,546 A | 12/1999 | Snow et al. | | 6,378,351 B1 | 4/2002 | Ouchi et al. |
| 6,010,512 A | 1/2000 | Chu et al. | | 6,383,196 B1 | 5/2002 | Leslie et al. |
| 6,013,095 A | 1/2000 | Ouchi et al. | | 6,383,197 B1 | 5/2002 | Conlon et al. |
| 6,019,733 A | 2/2000 | Farascioni | | 6,387,102 B2 | 5/2002 | Pagedas |
| 6,019,758 A | 2/2000 | Slater | | 6,391,043 B1 | 5/2002 | Moll et al. |
| 6,019,770 A | 2/2000 | Christoudias | | 6,394,964 B1 | 5/2002 | Sievert, Jr. et al. |
| 6,019,780 A | 2/2000 | Lombardo et al. | | 6,409,678 B1 | 6/2002 | Ouchi |
| 6,022,362 A | 2/2000 | Lee et al. | | 6,409,733 B1 | 6/2002 | Conlon et al. |
| 6,024,708 A | 2/2000 | Bales et al. | | 6,419,640 B1 | 7/2002 | Taylor |
| 6,036,656 A | 3/2000 | Slater | | 6,419,679 B1 | 7/2002 | Dhindsa |
| 6,036,698 A | 3/2000 | Fawzi et al. | | 6,425,910 B1 | 7/2002 | Hugueny et al. |
| 6,039,752 A | 3/2000 | Kimura et al. | | 6,427,509 B1 | 8/2002 | Ouchi et al. |
| RE36,666 E | 4/2000 | Honkanen et al. | | 6,432,064 B1 | 8/2002 | Hibrier et al. |
| 6,050,955 A | 4/2000 | Bryan et al. | | 6,436,054 B1 | 8/2002 | Viola et al. |
| 6,053,877 A | 4/2000 | Banik | | 6,436,117 B1 | 8/2002 | Waller et al. |
| 6,059,793 A | 5/2000 | Pagedas | | 6,440,085 B1 | 8/2002 | Krzyzanowski |
| 6,063,103 A | 5/2000 | Hashiguchi | | 6,461,310 B1 | 10/2002 | Palmer et al. |
| 6,068,603 A | 5/2000 | Suzuki | | 6,468,227 B2 | 10/2002 | Zimmon |
| 6,071,233 A | 6/2000 | Ishikawa et al. | | 6,485,436 B1 | 11/2002 | Truckai et al. |
| 6,071,248 A | 6/2000 | Zimmon | | 6,488,636 B2 | 12/2002 | Bryan et al. |
| 6,074,408 A | 6/2000 | Freeman | | 6,494,885 B1 | 12/2002 | Dhindsa |
| 6,077,230 A | 6/2000 | Gregoire et al. | | 6,514,197 B1 | 2/2003 | Ouchi et al. |
| 6,077,287 A | 6/2000 | Taylor et al. | | 6,514,269 B2 | 2/2003 | Yamamoto |
| RE36,795 E | 7/2000 | Rydell | | 6,517,498 B1 | 2/2003 | Burbank et al. |
| 6,083,150 A | 7/2000 | Aznoian et al. | | 6,520,968 B2 | 2/2003 | Bates et al. |
| 6,083,240 A | 7/2000 | Ouchi | | 6,527,781 B2 | 3/2003 | Bates et al. |
| 6,093,195 A | 7/2000 | Ouchi | | 6,530,891 B2 | 3/2003 | Miller |
| 6,099,483 A | 8/2000 | Palmer et al. | | 6,544,194 B1 | 4/2003 | Kortenbach et al. |
| 6,099,534 A | 8/2000 | Bates et al. | | 6,551,254 B2 | 4/2003 | Nishtalas et al. |
| 6,099,537 A | 8/2000 | Sugai et al. | | 6,554,850 B1 | 4/2003 | Ouchi et al. |
| 6,106,543 A | 8/2000 | Esser | | 6,561,988 B1 | 5/2003 | Turturro et al. |
| 6,110,127 A * | 8/2000 | Suzuki ............ 600/565 | | 6,565,591 B2 | 5/2003 | Brady et al. |
| 6,123,678 A | 9/2000 | Palmer et al. | | 6,569,105 B1 | 5/2003 | Kortenbach et al. |
| 6,129,683 A | 10/2000 | Sutton et al. | | 6,575,977 B1 | 6/2003 | Michelson |
| 6,139,508 A | 10/2000 | Simpson et al. | | 6,582,450 B2 | 6/2003 | Ouchi |
| 6,142,955 A | 11/2000 | Farascioni et al. | | 6,582,451 B1 | 6/2003 | Marucci |
| 6,142,956 A | 11/2000 | Kortenbach et al. | | 6,589,252 B2 | 7/2003 | McGuckin, Jr. |
| 6,142,957 A * | 11/2000 | Diamond et al. ............ 600/567 | | 6,605,104 B2 | 8/2003 | Sato et al. |
| 6,149,607 A | 11/2000 | Simpson et al. | | 6,607,227 B1 | 8/2003 | Morton |
| 6,152,924 A | 11/2000 | Parins | | 6,613,068 B2 | 9/2003 | Ouchi |

| | | |
|---|---|---|
| 6,616,662 B2 | 9/2003 | Scholer et al. |
| 6,620,111 B2 | 9/2003 | Stephens et al. |
| 6,626,915 B2 | 9/2003 | Leveille |
| 6,632,182 B1 | 10/2003 | Treat |
| 6,663,645 B2 | 12/2003 | Nishtala et al. |
| 6,673,092 B1 | 1/2004 | Bacher |
| 6,679,894 B2 | 1/2004 | Damarati |
| 6,685,723 B1 | 2/2004 | Duchi et al. |
| 6,689,122 B2 | 2/2004 | Yamamoto |
| 6,692,445 B2 | 2/2004 | Roberts et al. |
| 6,695,791 B2 | 2/2004 | Gonzalez |
| 6,709,445 B2 | 3/2004 | Boebel et al. |
| 6,736,781 B2 | 5/2004 | Lee |
| 6,736,813 B2 | 5/2004 | Yamauchi et al. |
| 6,740,106 B2 | 5/2004 | Kobayashi et al. |
| 6,743,185 B2 | 6/2004 | Weber et al. |
| 6,743,228 B2 | 6/2004 | Lee et al. |
| 6,752,822 B2 | 6/2004 | Jespersen |
| 6,767,349 B2 | 7/2004 | Ouchi |
| 6,792,663 B2 | 9/2004 | Krzyzanowski |
| 6,805,699 B2 | 10/2004 | Shimm |
| 6,808,491 B2 | 10/2004 | Kortenbach et al. |
| 6,951,560 B1 | 10/2005 | Kidooka |
| 6,969,389 B2 | 11/2005 | Kidooka |
| 7,033,315 B2 | 4/2006 | Smith |
| 7,037,276 B2 | 5/2006 | Sayet et al. |
| 7,052,489 B2 | 5/2006 | Griego et al. |
| 7,105,000 B2 | 9/2006 | McBrayer |
| RE39,415 E | 11/2006 | Bales et al. |
| 7,171,839 B2 | 2/2007 | Krzyzanowski |
| 7,186,261 B2 | 3/2007 | Prestel |
| 7,311,674 B2 | 12/2007 | Gingrich et al. |
| 7,326,209 B2 | 2/2008 | Kidooka |
| 7,341,564 B2 | 3/2008 | Zwiefel et al. |
| 7,354,439 B2 | 4/2008 | Kidooka |
| 7,422,592 B2 | 9/2008 | Morley et al. |
| 7,534,253 B2 | 5/2009 | Endara et al. |
| 7,621,910 B2 | 11/2009 | Sugi |
| 7,736,363 B2 | 6/2010 | Watnabe |
| 7,749,222 B2 | 7/2010 | Lu et al. |
| 7,775,989 B2 * | 8/2010 | Nakao ............ 600/564 |
| 2001/0000348 A1 | 4/2001 | Chu et al. |
| 2001/0009978 A1 | 7/2001 | Krueger et al. |
| 2001/0025149 A1 * | 9/2001 | Kobayashi et al. ........... 600/564 |
| 2001/0047124 A1 * | 11/2001 | Yamamoto ................ 600/101 |
| 2001/0051812 A1 | 12/2001 | Ouchi |
| 2001/0056248 A1 | 12/2001 | Zimmon |
| 2002/0013595 A1 | 1/2002 | Yamamoto |
| 2002/0022850 A1 | 2/2002 | McGuckin |
| 2002/0029006 A1 * | 3/2002 | Turturro et al. ............... 600/562 |
| 2002/0049442 A1 * | 4/2002 | Roberts et al. ................. 606/50 |
| 2002/0062131 A1 | 5/2002 | Gallo |
| 2002/0065474 A1 | 5/2002 | Viola |
| 2002/0068944 A1 | 6/2002 | White et al. |
| 2002/0082543 A1 * | 6/2002 | Park et al. ................. 604/21 |
| 2002/0095100 A1 | 7/2002 | Lee et al. |
| 2002/0111564 A1 | 8/2002 | Burbank et al. |
| 2002/0120211 A1 | 8/2002 | Wardle et al. |
| 2002/0143270 A1 | 10/2002 | Miller |
| 2002/0143353 A1 | 10/2002 | George et al. |
| 2002/0156395 A1 | 10/2002 | Stephens et al. |
| 2002/0165580 A1 | 11/2002 | Zniefel et al. |
| 2002/0193705 A1 | 12/2002 | Burbank et al. |
| 2002/0198466 A1 | 12/2002 | Alberico |
| 2003/0009193 A1 | 1/2003 | Corsaro |
| 2003/0040681 A1 | 2/2003 | Ng et al. |
| 2003/0050574 A1 | 3/2003 | Krueger |
| 2003/0073928 A1 | 4/2003 | Kortenbach et al. |
| 2003/0097146 A1 | 5/2003 | Montalvo et al. |
| 2003/0097147 A1 | 5/2003 | Prestel |
| 2003/0105402 A1 | 6/2003 | Lee |
| 2003/0120281 A1 | 6/2003 | Bates et al. |
| 2003/0125639 A1 | 7/2003 | Fisher et al. |
| 2003/0144605 A1 | 7/2003 | Burbank et al. |
| 2003/0163129 A1 | 8/2003 | Lee et al. |
| 2003/0191413 A1 | 10/2003 | Damaratu |
| 2003/0191464 A1 | 10/2003 | Kidooka |
| 2003/0195432 A1 | 10/2003 | Kortenbach et al. |
| 2003/0199811 A1 | 10/2003 | Sage et al. |
| 2003/0212342 A1 | 11/2003 | Rudnick et al. |
| 2003/0229293 A1 | 12/2003 | Hibner et al. |
| 2004/0015165 A1 | 1/2004 | Kidooka |
| 2004/0024333 A1 | 2/2004 | Brown |
| 2004/0034310 A1 | 2/2004 | McAlister et al. |
| 2004/0059345 A1 | 3/2004 | Nakao et al. |
| 2004/0068291 A1 | 4/2004 | Suzuki |
| 2004/0087872 A1 | 5/2004 | Anderson et al. |
| 2004/0087979 A1 | 5/2004 | Field et al. |
| 2004/0092967 A1 | 5/2004 | Sancoff et al. |
| 2004/0093019 A1 | 5/2004 | Kothe |
| 2004/0097829 A1 | 5/2004 | McRury et al. |
| 2004/0098040 A1 | 5/2004 | Taniguchi et al. |
| 2004/0122461 A1 | 6/2004 | McGuire et al. |
| 2004/0138587 A1 | 7/2004 | Lyons |
| 2004/0186348 A1 | 9/2004 | Kidooka |
| 2004/0199159 A1 | 10/2004 | Lee et al. |
| 2004/0220496 A1 | 11/2004 | Gonzalez |
| 2004/0243024 A1 | 12/2004 | Kortenbach et al. |
| 2004/0254592 A1 | 12/2004 | DiCarlo et al. |
| 2004/0260198 A1 | 12/2004 | Rothberg et al. |
| 2004/0260337 A1 | 12/2004 | Freed |
| 2005/0033354 A1 | 2/2005 | Montalvo et al. |
| 2005/0043758 A1 | 2/2005 | Golden et al. |
| 2005/0216036 A1 * | 9/2005 | Nakao ............ 606/142 |
| 2005/0240218 A1 | 10/2005 | Freed et al. |
| 2006/0025780 A1 | 2/2006 | James |
| 2006/0149222 A1 | 7/2006 | Okada |
| 2006/0184198 A1 | 8/2006 | Bales et al. |
| 2006/0206145 A1 | 9/2006 | Griego et al. |
| 2006/0258954 A1 | 11/2006 | Timberlake et al. |
| 2007/0055172 A1 | 3/2007 | Ratnakar |
| 2007/0078458 A1 | 4/2007 | Dumbauld et al. |
| 2007/0149971 A1 | 6/2007 | Nishimura |
| 2007/0198011 A1 | 8/2007 | Sugita |
| 2007/0244507 A1 | 10/2007 | Szweda et al. |
| 2007/0244508 A1 | 10/2007 | Weizman et al. |
| 2007/0244509 A1 | 10/2007 | Weizman et al. |
| 2007/0244510 A1 | 10/2007 | Weizman et al. |
| 2007/0244511 A1 | 10/2007 | Weizman et al. |
| 2007/0244512 A1 | 10/2007 | Messamer |
| 2007/0244513 A1 | 10/2007 | Weizman et al. |
| 2007/0244514 A1 | 10/2007 | Weizman et al. |
| 2008/0064982 A1 | 3/2008 | Nowlin et al. |
| 2008/0125769 A1 | 5/2008 | Suzuki et al. |
| 2008/0171908 A1 | 7/2008 | Okada et al. |
| 2008/0194910 A1 | 8/2008 | Miyamoto et al. |
| 2009/0012422 A1 * | 1/2009 | Marban ................ 600/564 |
| 2009/0088738 A1 | 4/2009 | Guerra et al. |
| 2009/0088739 A1 | 4/2009 | Hushka et al. |
| 2009/0088740 A1 | 4/2009 | Guerra et al. |
| 2009/0088741 A1 | 4/2009 | Hushka et al. |
| 2009/0088744 A1 | 4/2009 | Townsend |
| 2009/0088745 A1 | 4/2009 | Hushka et al. |
| 2009/0088746 A1 | 4/2009 | Hushka et al. |
| 2009/0088747 A1 | 4/2009 | Hushka et al. |
| 2009/0131932 A1 | 5/2009 | Vakharia et al. |
| 2009/0131933 A1 | 5/2009 | Ghabrial et al. |
| 2009/0216078 A1 | 8/2009 | Iwanaga et al. |
| 2009/0264918 A1 | 10/2009 | Endara et al. |
| 2009/0287112 A1 | 11/2009 | Freeman |
| 2010/0106068 A1 | 4/2010 | Karpiel et al. |

FOREIGN PATENT DOCUMENTS

| | | |
|---|---|---|
| DE | 85 32 644 | 5/1986 |
| DE | 87 12 328 U1 | 3/1988 |
| DE | 88 14 560 | 3/1989 |
| DE | 39 20 706 | 1/1991 |
| DE | 40 06 673 | 9/1991 |
| DE | 40 12 882 | 10/1991 |
| DE | 296 14 931 | 3/1997 |
| DE | 199 04 723 | 8/1999 |
| DE | 100 49 592 | 5/2001 |
| DE | 103 16 132 | 10/2003 |
| EP | 0 279 358 B1 | 8/1988 |
| EP | 0 317 526 | 5/1989 |
| EP | 0 507 620 | 10/1992 |
| EP | 0 585 921 | 3/1994 |
| EP | 1 240 870 | 9/2002 |

| | | | | | | |
|---|---|---|---|---|---|---|
| EP | 1 252 863 | 10/2002 | | JP | 2002-017734 | 1/2002 |
| EP | 1 348 378 | 10/2003 | | JP | 2002-034989 | 2/2002 |
| EP | 1 872 730 | 1/2008 | | JP | 2002-45363 | 2/2002 |
| EP | 1 875 872 | 1/2008 | | JP | 2002-119514 | 4/2002 |
| FR | 2 805 146 A | 8/2001 | | JP | 2002-165754 | 6/2002 |
| JP | 2 001251 | 1/1990 | | JP | 2002-191605 | 7/2002 |
| JP | 03-139340 | 6/1991 | | JP | 2002-191606 | 7/2002 |
| JP | 04-307050 | 10/1992 | | JP | 2002-282265 | 10/2002 |
| JP | 05-031120 | 2/1993 | | JP | 2002-330973 | 11/2002 |
| JP | 05-220157 | 8/1993 | | JP | 2003-93393 | 4/2003 |
| JP | 05-237120 | 9/1993 | | JP | 2003-126103 | 5/2003 |
| JP | 05-309097 | 11/1993 | | JP | 2003-299669 | 10/2003 |
| JP | 06-114063 | 4/1994 | | JP | 2003-310635 | 11/2003 |
| JP | 06-217987 | 8/1994 | | JP | 2004-97615 | 4/2004 |
| JP | 08-224242 | 9/1996 | | JP | 2004-229976 | 8/2004 |
| JP | 09-075356 | 3/1997 | | JP | 2005-058344 | 3/2005 |
| JP | 09-98978 | 4/1997 | | JP | 2005-193061 | 7/2005 |
| JP | 09-215747 | 8/1997 | | JP | 2005-237431 | 9/2005 |
| JP | 09-276282 | 10/1997 | | JP | 2006-296578 | 11/2006 |
| JP | 09-276285 | 10/1997 | | JP | 2006-296781 | 11/2006 |
| JP | 10-024045 | 1/1998 | | JP | 2006-334267 | 12/2006 |
| JP | 10-028692 | 2/1998 | | JP | 2006-334348 | 12/2006 |
| JP | 10-118015 | 5/1998 | | JP | 2007-260248 | 10/2007 |
| JP | 10-118076 | 5/1998 | | JP | 2007-330436 | 12/2007 |
| JP | 10-118091 | 5/1998 | | JP | 2009-153535 | 7/2009 |
| JP | 10-137246 | 5/1998 | | JP | 2009-297503 | 12/2009 |
| JP | 10-137250 | 5/1998 | | WO | WO/90/01297 | 2/1990 |
| JP | 10-137251 | 5/1998 | | WO | WO 93/20754 | 10/1993 |
| JP | 10-165408 | 6/1998 | | WO | WO 94/17741 | 8/1994 |
| JP | 11-19086 | 1/1999 | | WO | WO/94/26172 | 11/1994 |
| JP | 11-19087 | 1/1999 | | WO | WO/94/26181 | 11/1994 |
| JP | 11-033032 | 2/1999 | | WO | WO/95/20914 | 8/1995 |
| JP | 11-047135 | 2/1999 | | WO | WO/96/24289 | 8/1996 |
| JP | 11-076244 | 3/1999 | | WO | WO 97/11643 | 4/1997 |
| JP | 11-155877 | 6/1999 | | WO | WO/98/26723 | 6/1998 |
| JP | 11-178829 | 7/1999 | | WO | WO/98/35615 | 8/1998 |
| JP | 11-239582 | 9/1999 | | WO | WO/99/15073 | 4/1999 |
| JP | 2000-189429 | 7/2000 | | WO | WO/99/20096 | 4/1999 |
| JP | 2000-189430 | 7/2000 | | WO | WO/99/53851 | 10/1999 |
| JP | 2000 189431 | 7/2000 | | WO | WO/01/28427 A1 | 4/2001 |
| JP | 2000-189433 | 7/2000 | | WO | WO/02/062226 | 8/2002 |
| JP | 2000-189435 | 7/2000 | | WO | WO/02/062227 | 8/2002 |
| JP | 2000-189432 | 10/2000 | | WO | WO/03/082119 | 10/2003 |
| JP | 2000-271128 | 10/2000 | | WO | WO/03/082122 | 10/2003 |
| JP | 2000-279418 | 10/2000 | | WO | WO/2004/010874 | 2/2004 |
| JP | 2000-296131 | 10/2000 | | WO | WO 2006/114952 | 11/2006 |
| JP | 2001-095807 | 4/2001 | | WO | WO 2006/114989 | 11/2006 |
| JP | 2001-104318 | 4/2001 | | | | |
| JP | 2001-029349 | 6/2001 | | | | |
| JP | 2001-190556 | 7/2001 | | | | |
| JP | 2002-011014 | 1/2002 | | | | |

OTHER PUBLICATIONS

English language translation of DE 87 12 328 (4 pages).

* cited by examiner

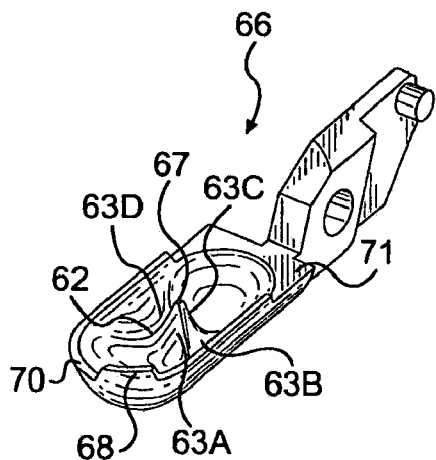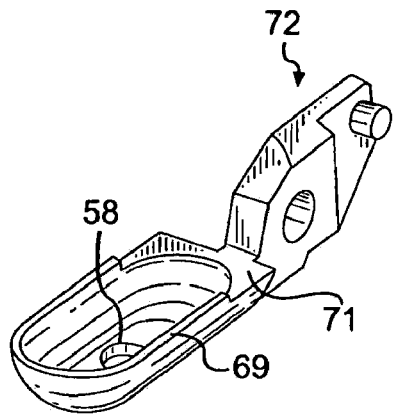
FIG. 10A  FIG. 10B
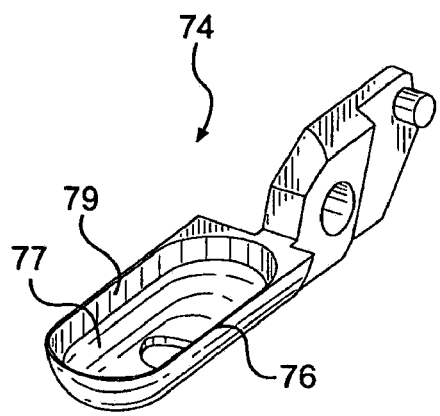
FIG. 10C
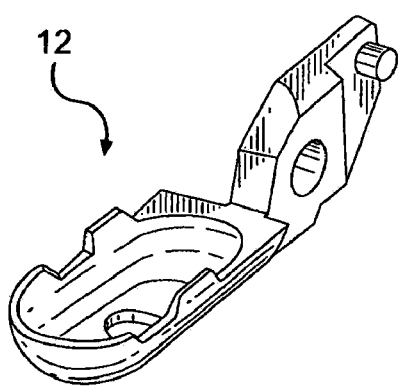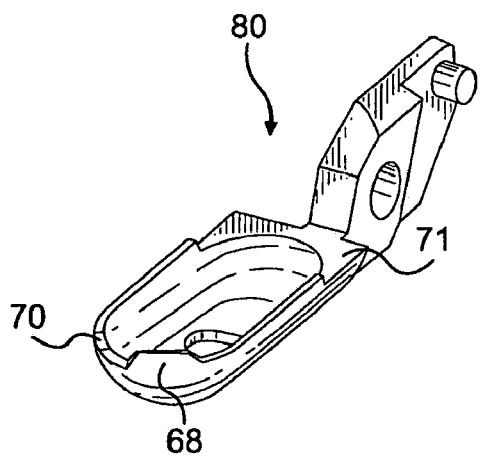
FIG. 10D  FIG. 10E

BIOPSY FORCEPS ASSEMBLIES

CROSS-REFERENCE TO RELATED APPLICATION

This application is a continuation of U.S. application Ser. No. 11/128,319, filed May 13, 2005 now U.S. Pat. No. 7,762,960, which is incorporated herein by reference in its entirety.

FIELD OF THE INVENTION

The invention relates to biopsy forceps assemblies for acquiring tissue samples from a desired body portion. For example, embodiments of the invention may include miniature biopsy forceps assemblies for acquiring tissue samples from desired body portions in order to assist in diagnosis of anatomical diseases and disorders, such as cancer.

BACKGROUND OF THE INVENTION

A biopsy entails the surgical removal of tissue or cells from the body of a patient for pathological examination of the collected sample. The purpose for taking a biopsy sample is often to look for cellular shape changes represented in the collected sample. The identification of particular cellular shape changes in a collected specimen can be instrumental in the identification of cancer in a patient.

Biopsy tissue samples are required for the diagnosis and treatment of a wide range of diseases and disorders that often require a physician to access the tortuous and relatively small cross-sectional areas of a patient's internal anatomical body lumens. A patient's pancreaticobiliary system (including the anatomical regions of the gall bladder, pancreas, and the biliary tree), for example, is accessed for retrieval of biopsy samples for the treatment of disorders of certain portions of the digestive system.

The biliary system delivers bile produced by the liver to the duodenum where the bile assists other gastric fluids in digesting food. The biliary system includes the liver, as well as a plurality of bodily channels and organs that are disposed between the liver and the duodenum. Within the liver lobules, there are many fine "bile canals" that receive secretions from the hepatic cells. The canals of neighboring lobules unite to form larger ducts, and these converge to become the "hepatic ducts." They merge, in turn, to form the "common hepatic duct." The "common bile duct" is formed by the union of the common hepatic and the cystic ducts. It leads to the duodenum, where its exit is guarded by a sphincter muscle. This sphincter normally remains contracted until the bile is needed, so that bile collects in the common bile duct and backs up to the cystic duct. When this happens, the bile flows into the gallbladder and is stored there. Sometimes, however, lesions may grow in portions of the biliary system, for example, one of the biliary ducts, that impede bile from properly flowing through the system. In some cases, the lesions may completely prevent the bile flow. This is undesirable as it interrupts the regular digestive process and may even cause damage to the channels and organs of the biliary system.

In order to properly treat the lesions, it is sometimes necessary to acquire a biopsy tissue sample from the lesion, analyze the sample, and then determine a proper treatment based on the analysis, such as, for example, chemotherapy for the treatment of a cancerous mass.

Endoscopes are often used to access and visualize a patient's anatomical lumen, such as those in the pancreaticobiliary system, during a medical procedure. Once the endoscope is positioned in the desired body portion, a biopsy instrument can be advanced through the working channel of the endoscope to the desired body portion. The endoscope and biopsy instrument may then be manipulated as desired for visualization and specimen sampling respectively.

Smaller diameter endoscopes are presently available in the endoscopy market that help reduce unnecessary trauma to the tissues of a patient and provide more versatile endoscopes capable of accessing more diverse categories of patient body lumens. With these smaller diameter endoscopes comes necessarily smaller working channels, which limit the size of any auxiliary instrument used. This, in turn, limits the size of any biopsy specimen collected.

Biopsies are often performed with a biopsy instrument having forceps with two jaws activated by an internal manipulating wire or wires. The instrument is passed through an endoscope to a desired location and then the jaws are closed to grab and sever the biopsy sample. The instrument with the detached specimen is then withdrawn from the endoscope so that the sample is removed. Frequently, due to a small moment arm of the instrument, the cutting, biting, shearing, or tearing force of the jaws is not sufficient or the jaws are not sharp enough (often due to machining tolerances imposed on small diameter elements) to cleanly shear the tissue which is then torn off by a pulling movement. This is particularly problematic in smaller diameter endoscopes with smaller diameter working channels. Accordingly, additional structural jaw features are desired that allow for improved tissue retrieval and improved sample retention, particularly where the desired treatment lumen is of a relatively small cross-section and/or the working channel of the endoscope is relatively small.

Thus, it is desirable to have a miniature biopsy forceps assembly that can access small working channels of smaller endoscopic devices, more precisely access the tortuous and relatively small cross-sectional areas of certain anatomical body lumens, and both sever and retain tissue samples adequate for pathology study.

SUMMARY OF THE INVENTION

Embodiments of the present invention are directed to medical devices for obtaining tissue samples that obviate one or more of the limitations and disadvantages of prior medical devices.

In one embodiment, a device for obtaining a tissue sample include a proximal actuator and a distal assembly having first and second opposing jaws. The first jaw includes a first curved distal edge defining only one tooth offset from a center of the first curved distal edge and an inner surface defining a substantially pyramid-shaped spike. The second jaw includes a second curved distal edge defining only one tooth offset from a center of the second curved distal edge and a concave inner surface defining at least one hole. An elongate member connects the proximal actuator to the distal assembly wherein actuation of the proximal actuator causes the first and second jaws to pivot relative to one another.

According to another embodiment, a device for obtaining a tissue sample includes a proximal actuator and a distal assembly having first and second opposing jaws. A cup portion of the first jaw defines an aperture and an edge of the aperture is raised above an inner surface of the cup portion adjacent the aperture. An elongate member connects the proximal actuator to the distal assembly wherein actuation of the proximal actuator causes the first and second jaws to pivot relative to one another.

According to another embodiment, a device for obtaining a tissue sample includes a proximal actuator, a distal assembly having first and second opposing jaws, wherein the first jaw includes lateral, straight edges having teeth, the lateral edges connected by a curved distal edge not including teeth. An elongate member connects the proximal actuator to the distal assembly and wherein actuation of the proximal actuator causes the first and second jaws to pivot relative to one another.

In various embodiments, the device may include one or more of the following additional features: wherein the second jaw includes lateral, straight edges having teeth, the lateral edges of the second jaw connected by a curved distal edge not including teeth; wherein a pattern of teeth arranged on the first jaw complements a pattern of teeth arranged on the second jaw such that, when the jaws are closed, the edges of the first and second jaws align substantially without space between the edges; wherein each tooth projecting from the lateral, straight edges of the first and second jaws includes a substantially flat top surface and angled sides; wherein each jaw includes two teeth on one lateral, straight edge and only one tooth on an opposite, lateral, straight edge; wherein a proximal portion of each jaw includes a stepped-down heel portion to permit substantially complete jaw closure; wherein each jaw includes a concave inner surface defining a substantially hemispherical cup; wherein the concave inner surface of the first jaw defines at least one hole; wherein the inner concave surface of the first jaw defines a frusto-conical shaped projection having a center defining a hole; wherein one of the first jaw and the second jaw includes a substantially conical-shaped spike that points towards the other of the first jaw and second jaw; wherein a concave inner surface of the other of the first jaw and the second jaw defines a hole aligned opposite the substantially conical-shaped spike when the first and second jaws are in a closed position; wherein one of the first jaw and the second jaw includes a substantially pyramid-shaped spike that points towards the other of the first jaw and the second jaw; wherein the substantially pyramid-shaped spike includes triangular-shaped faces that meet at a point; wherein an inner surface of the one of the first jaw and the second jaw defines distinct concave surfaces on distal, proximal, and lateral sides of the substantially pyramid-shaped spike; wherein the tip of the substantially pyramid-shaped spike terminates to form a substantially flat square shape; and wherein at least one of the first and second jaws is electrically conductive and configured to act as an electrode for conducting current to tissue.

According to another embodiment of the invention, a device for obtaining a tissue sample includes a proximal actuator, a distal assembly having first and second jaws, wherein the first jaw includes an inner surface defining a substantially pyramid-shaped spike. An elongate member connects the proximal actuator to the distal assembly and actuation of the proximal actuator causes the first and second jaws to pivot relative to one another.

In various embodiments, the device may include one or more of the following additional features: wherein each jaw includes a concave inner surface defining a substantially hemispherical cup; wherein the concave inner surface of the second jaw defines a hole; wherein the inner concave surface of the second jaw defines a frusto-conical shaped projection having a center defining a hole; wherein the hole is aligned opposite the substantially pyramid-shaped spike when the first and second jaws are in a closed position; wherein the substantially pyramid-shaped spike includes a point directed towards the second jaw; wherein the substantially pyramid-shaped spike includes triangular-shaped faces that meet at a point; wherein the inner surface of the first jaw defines distinct concave surfaces on distal, proximal, and lateral sides of the substantially pyramid-shaped spike; wherein the substantially pyramid-shaped spike is integrally formed with the first jaw; wherein the first jaw includes lateral, straight edges having teeth, the lateral edges connected by a curved distal edge not including teeth; wherein the second jaw includes lateral, straight edges having teeth, the lateral edges of the second jaw connected by a curved distal edge not including teeth; wherein a pattern of teeth arranged on the first jaw complements a pattern of teeth arranged on the second jaw such that, when the jaws are closed, the edges of the first and second jaws align substantially without space between the edges; wherein each tooth projecting from the lateral, straight edges of the first and second jaws includes a substantially flat top surface and angled sides; wherein each jaw includes two teeth on one lateral, straight edge and only one tooth on an opposite, lateral, straight edge; and wherein a proximal portion of each jaw includes a stepped-down heel portion to permit substantially complete jaw closure.

According to another embodiment of the invention, a device for obtaining a tissue sample includes a proximal actuator and a distal assembly having first and second jaws. The first jaw includes a concave inner surface defining a substantially hemispherical cup and wherein a tissue retention element protrudes from the inner surface at a distal end of the cup. An elongate member connects the proximal actuator to the distal assembly and wherein actuation of the proximal actuator causes the first and second jaws to pivot relative to one another.

In various embodiments, the device may include one or more of the following additional features: wherein the second jaw includes a concave inner surface defining a substantially hemispherical cup, wherein a tissue retention element protrudes from the inner surface of the second jaw at a distal end of the cup; wherein the tissue retention element includes at least one ramp that inclines upwardly toward a distal end of the jaw; wherein the tissue retention element includes a flat proximally directed face protruding from the inner surface of the hemispherical cup; wherein the tissue retention element extends from a distal portion of the inner surface of the jaw and forms a substantially flat surface within the cup; wherein the tissue retention element includes an inclined, proximally directed lip; and wherein the lip includes a flat upper surface integral with a distal edge of the cup; wherein the tissue retention element comprises a raised frusto-conical shaped projection having a center defining a hole; and wherein the tissue retention element comprises a plurality of curved fins.

According to another embodiment of the invention, a medical device includes a distal assembly having first and second end effectors and a proximal actuator having first and second portions that move relative to one another. The relative movement of the first and second portions causes the first and second end effectors to pivot relative to one another. An elongate tubular member defining a lumen therein and connects the first portion of the actuator to the distal assembly. A wire extends within the lumen of the elongate tubular member and connects the second portion of the actuator to the first and second end effectors. A tube within the actuator is movable with the second portion of the actuator and configured to receive the wire therein so that axial movement of the tube causes corresponding axial movement of the wire.

In various embodiments, the device may include one or more of the following additional features: wherein the tube includes a bent portion received by the second portion of the actuator; wherein the bent portion retains the wire within the tube; wherein the wire is retained in the tube without affixing the wire to the tube; wherein the wire is retained in the tube through a friction fit or a geometric fit; wherein the tube is a hypotube; wherein the end effectors are jaws for obtaining a tissue sample; a retainer within the first portion of the proximal actuator affixing the elongate tubular member to the first portion of the actuator; wherein the first portion of the actuator is hollow and defines a lumen housing the retainer such that longitudinal movement of the retainer within the first portion of the actuator is prevented; wherein longitudinal movement of the retainer is prevented by flanges along the retainer configured to mate with corresponding grooves formed in the actuator lumen; wherein a proximal end of the elongate tubular member attaches along an exterior of a reduced diameter distal portion of the retainer; wherein the tube is received within the retainer and moves relative to the retainer; wherein the bent portion forms an S-shaped, L-shaped, Z-shaped, or circular configuration; wherein a portion of the wire includes a layer of polymeric coating; wherein a proximal-most portion and a distal-most portion of the wire remains uncoated; and wherein an exterior surface of the elongate tubular member includes a polymeric coating.

According to another embodiment of the invention, a medical device includes a proximal actuator and a distal assembly. The distal assembly has a movable jaw and a fixed jaw, which includes a sharp distal point. An elongate member connects the proximal actuator to the distal assembly and wherein actuation of the proximal actuator causes the movable jaw to pivot relative to the fixed jaw.

In various embodiments, the device may include one or more of the following additional features: wherein the fixed jaw includes an outer perimeter defining cutting edges that extend distally to meet at the sharp point; wherein the movable jaw includes cutting edges that complement the cutting edge of the fixed jaw such that, when the movable jaw is closed, the cutting edges of the movable jaw and the fixed jaw align substantially without space between the cutting edges; wherein an inner surface of the fixed jaw includes an arch shaped concave indentation; wherein the movable jaw includes a triangular-shaped cutting perimeter; wherein a distal end of the movable jaw includes a flat distally directed surface; wherein the movable jaw defines an inner concave surface retaining a severed tissue sample; wherein the fixed jaw is integrally formed with a clevis defining a pivot hole about which the movable jaw pivots upon actuation of the proximal actuator; wherein the fixed jaw comprises a projection that narrows to a tissue penetrating needle tip; wherein the projection includes a concave inner surface that aids in the retention of tissue after the needle tip penetrates targeted tissue; and a wire extending through the elongate member for coupling the movable jaw to the proximal actuator, and wherein the movable jaw connects to the wire by a pair of links.

According to another embodiment of the invention, a medical device includes a proximal actuator and a distal assembly having first and second opposing jaws. The first jaw includes a first curved distal edge defining only one tooth offset from a center of the first curved distal edge. An elongate member connects the proximal actuator to the distal assembly and wherein actuation of the proximal actuator causes the first and second jaws to pivot relative to one another.

In various embodiments, the device may include one or more of the following additional features: wherein the outer surface of the tooth is curved; wherein the second jaw includes a second curved distal edge defining only one tooth offset from a center of the second curved distal edge; wherein the one tooth of first jaw and the one tooth of the second jaw are offset to opposite sides of the center of their respective curved distal edges; wherein the first jaw includes a recess to receive the tooth of the second jaw and the second jaw includes a recess to receive the tooth of the first jaw; and wherein each tooth includes a substantially flat top surface and angled sides.

According to another embodiment of the invention, a device for obtaining a tissue sample includes a proximal actuator and a distal assembly having first and second jaws. The first jaw includes a concave inner surface defining a substantially hemispherical cup. A curved spike protrudes from the inner surface at a distal end of the cup. The device further includes an elongate member connecting the proximal actuator to the distal assembly. Actuation of the proximal actuator causes the first and second jaws to pivot relative to one another.

In various embodiments, the device may include one or more of the following additional features: wherein the spike terminates in a sharp tip; wherein the spike curves in a proximal direction from a base of the spike; wherein the second jaw includes a concave inner surface defining at least one hole; and wherein the second jaw includes a concave inner surface defining a frusto-conical shaped projection, the projection having a center defining a hole.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

FIGS. 10A-10E illustrate various alternative structural arrangements for the upper and lower forceps jaws according to embodiments of the present invention.

DESCRIPTION OF THE EMBODIMENTS

Reference will now be made in detail to the exemplary embodiments of the invention, examples of which are illustrated in the accompanying drawings. Wherever possible, the same reference numbers will be used throughout the drawings to refer to the same or like parts.

According to exemplary embodiments, the invention relates to a forceps assembly for severing and retaining tissue samples. In embodiments that use the forceps assembly in an endoscopic medical procedure, the forceps assembly can be advanced through a working channel of an endoscope, including an endoscope specifically designed and/or sized for use with the forceps assembly, and into a tissue tract. When proximate a targeted tissue site, the forceps assembly can apply a separation force to tissue and thereby retain a biopsy sample. The forceps assembly is then retracted from the tissue tract through the working channel of the endoscope. For purposes of this disclosure, "separation" of tissue refers to the action applied by the forceps assembly to capture a tissue sample. Separation includes, but is not limited to, the cutting, biting, punching, tearing, and shearing applied by the jaws of the current forceps assembly.

In one exemplary aspect of the present invention, the biopsy forceps is designed to have an outer diameter ranging from approximately 0.5 mm to approximately 2 mm when the jaws are in the closed jaw position. Such a relatively small profile in the closed jaw position facilitates access within smaller working channels of endoscopic devices, such as, for example, access through working channels having an inner diameter as small as about 1.2 mm. In addition, such a relatively small profile forceps device facilitates maneuverability and precise access throughout the tortuous and relatively small cross-sectional areas of certain anatomical body lumens, such as, for example, a patient's pancreaticobiliary system.

Figure 1:
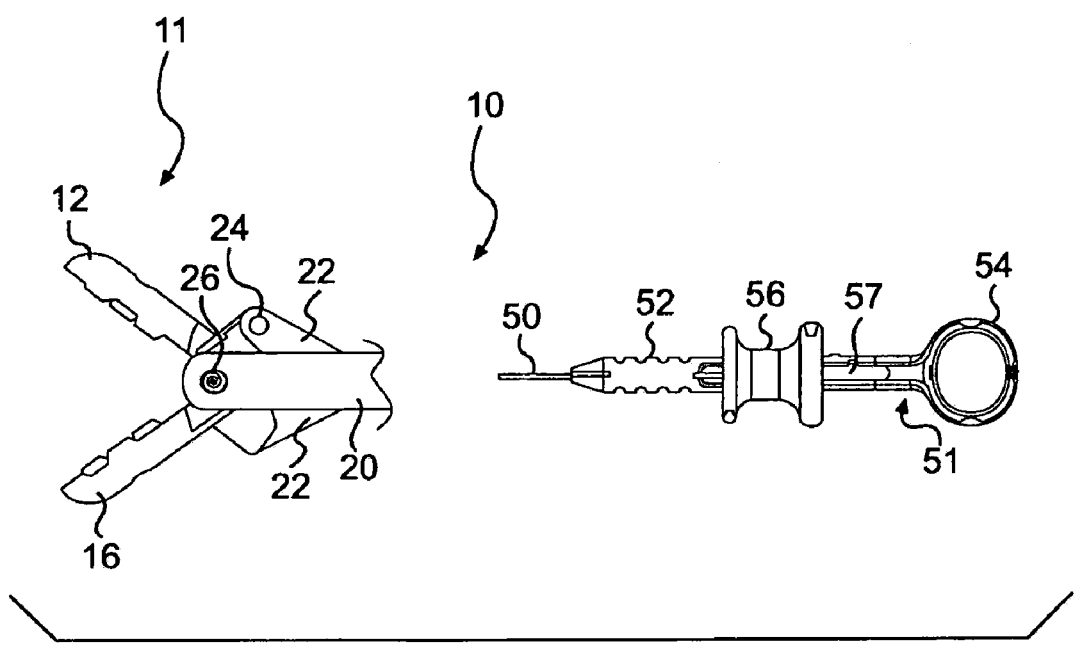
FIG. 1 is a fragmentary side view of a forceps assembly illustrating a proximal actuator and jaws in an open position according to an embodiment of the present invention.

An embodiment of a forceps assembly according to the present invention is depicted in FIG. 1. The forceps assembly 10 includes a distal end effector assembly 11, a proximal actuator 51, and an elongate member 50 connecting the distal assembly 11 with the proximal actuator 51. The size of the distal assembly 11 relative to the remaining components of assembly 10 in FIG. 1 has been exaggerated for the purposes of explanation and clarity and is not to be taken as literally representing the proper scale of the components.

The main components of the distal assembly include an upper jaw 12, a lower jaw 16, a clevis 20, and a pair of links 22. The main components of the proximal actuator 51 include an elongate handle 52 having a proximal thumb ring 54, and a spool 56 that slides relative to handle 52. The elongate member 50 is a tubular member that houses a core wire 39 (see FIG. 3D) that extends from the actuator 51 to the distal assembly 11. For purposes of this disclosure, "distal" refers to the end further from the device operator during use and "proximal" refers to the end closer to the device operator during use. Each of these components and their interconnection will now be described.

Figure 2A:
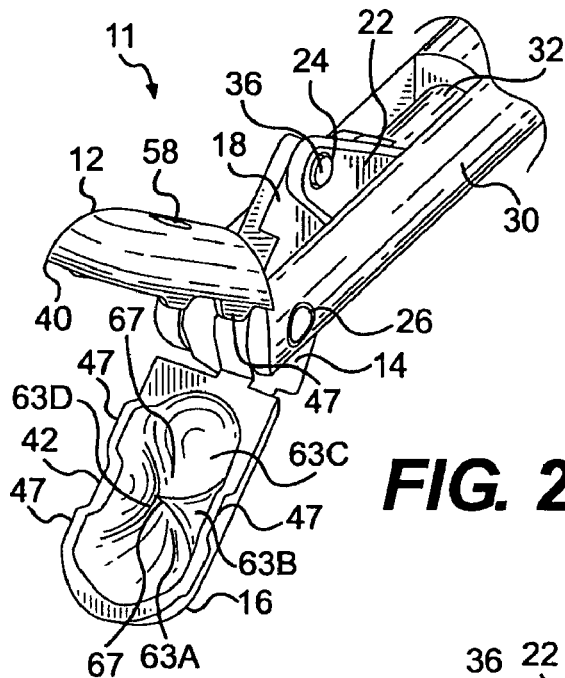
FIG. 2A is a perspective view of the distal end of a forceps assembly illustrating jaws in an open position according to an embodiment of the present invention.
Figure 2B:
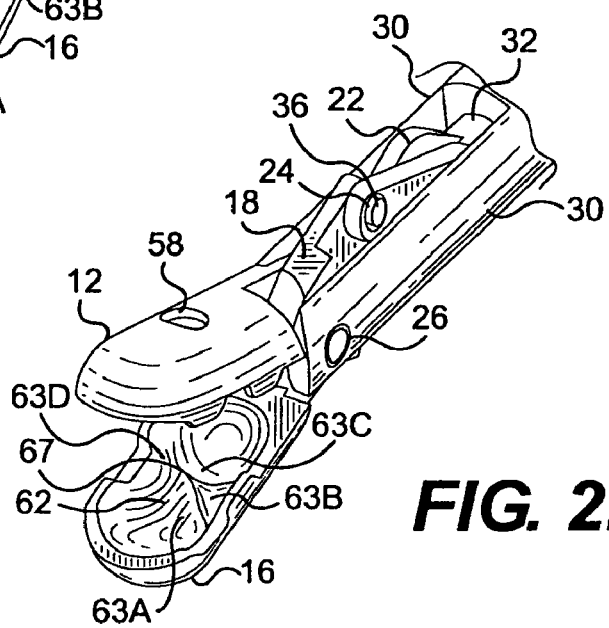
FIG. 2B is a perspective view of the forceps assembly of FIG. 2A, illustrating the jaws in a position midway between an open position and a closed position.
Figure 2C:
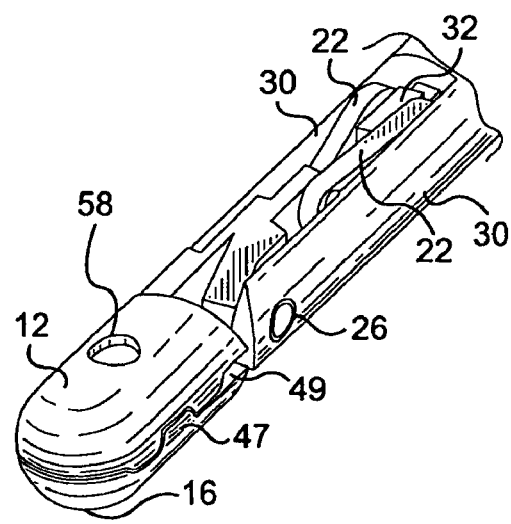
FIG. 2C is a perspective view of the forceps assembly of FIG. 2A illustrating the jaws in a closed position.

FIGS. 2A-C illustrate the distal assembly 11 with jaws 12, 16 in fully open, partially open, and closed positions, respectively. Upper jaw 12 includes a unitary proximal tang 14 defining a mounting bore 34 (shown more clearly in the FIG. 9 embodiment) and having a boss or link pin 36. Lower jaw 16 includes a unitary proximal tang 18 also defining a mounting bore 34 and having a boss or link pin 36. Link pins 36 extend perpendicular to, and away from, a central axis of forceps assembly 10.

Figure 3A:
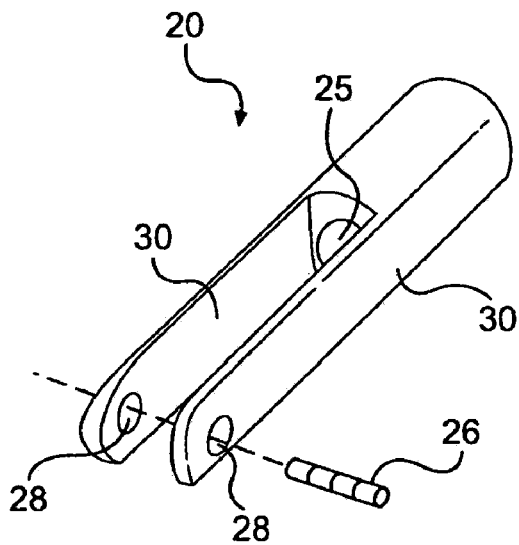
FIG. 3A is a perspective view of a clevis element according to an embodiment of the present invention.
Figure 3B:
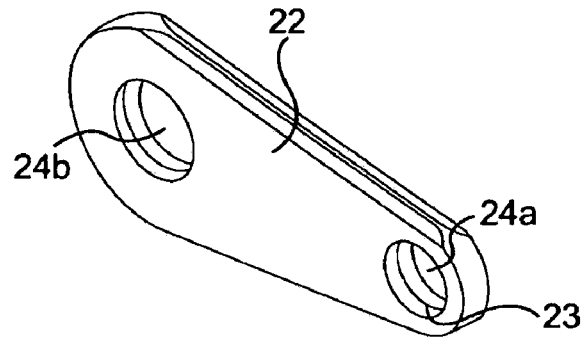
FIG. 3B is a perspective view of an individual jaw link element according to an embodiment of the present invention.
Figure 3C:
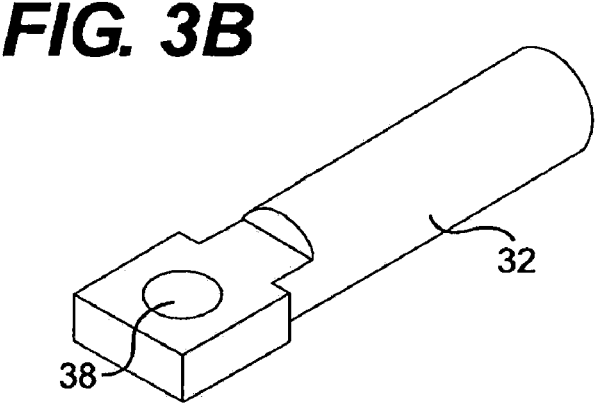
FIG. 3C is a perspective view of a core wire attachment element according to an embodiment of the present invention.

As shown in FIG. 3A, clevis 20 is generally hollow and has a U-shaped configuration. Clevis 20 includes a pair of arms 30 at a distal end a generally cylindrical proximal portion 21. The generally cylindrical proximal portion 21 is hollow and defines a lumen 25 extending therethrough for receiving a core wire attachment 32 (see FIGS. 2A-C, 3C, and 3E) configured for connection to the distal end of core wire 39 that causes actuation of the distal assembly 11. Each arm 30 has a generally curved outer surface and a generally flat inner surface. Each arm 30 defines an axle hole 28 that receives an end of an axle pin 26. Jaws 12, 16 insert between clevis arms 30. Axle pin 26 extends through axle holes 28 of arms 30 and mounting bore 34 of each jaw 12, 16, to connect jaws 12, 16 to clevis 30 and permit pivotal movement of jaws 12, 16 relative to one another and clevis 20. As seen in FIG. 1 and FIG. 3B, each link 22 defines a through-hole 24 at each of the proximal and distal ends of link 22. The distal through-hole 24a of each link 22 receives a boss or link pin 36 of a corresponding jaw 12, 16. A linking pin (not shown) extends through the proximal through-hole 24b of each link 22 and through the distal through-hole 38 of core wire attachment 32, thereby connecting the links 22 to attachment 32. The core wire attachment 32 extends through the clevis lumen 25 and connects to a distal end of the core wire 39 housed within elongate member 50. These connections couple the distal assembly 11 with the proximal actuator 51. The core wire 39 and attachment 32 are used to actuate the links 22 and the jaws 12, 16.

The distal through-hole 24a of links 22 can be machined to include a raised bevel 23 along the inner surface of the through-hole 24a in order to provide a countersink where the connection of link pins 36 and link 22 is completed through riveting. In contrast, where connection by riveting is not required, the proximal through-hole 24b does not include a raised bevel and instead has a constant diameter. An actuation drive mechanism is formed by the above-described interconnection of upper jaw 12, lower jaw 16, clevis 20, links 22, and core wire attachment 32.

Figure 3D:
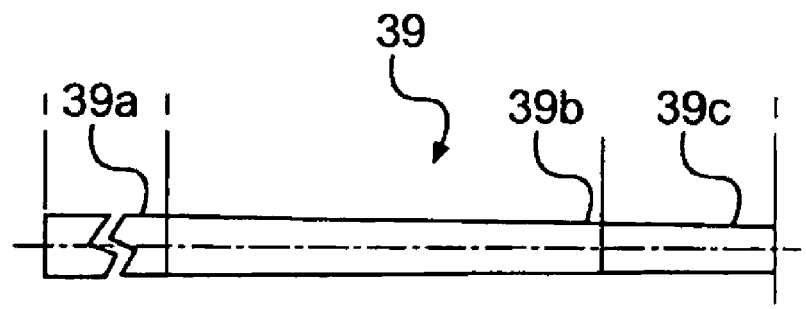
FIG. 3D is a fragmentary side view of a core wire element according to an embodiment of the present invention.
Figure 3E:
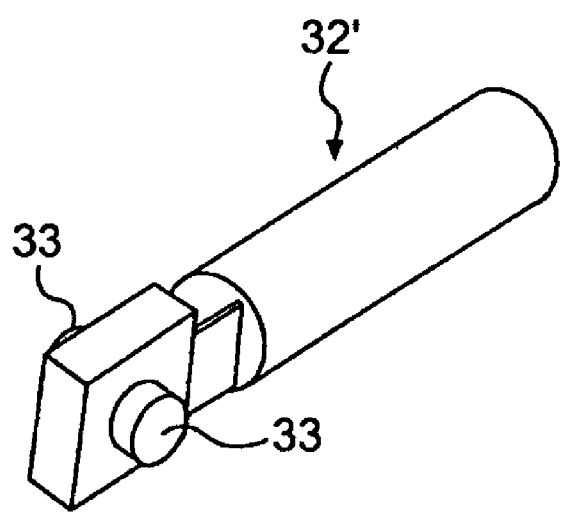
FIG. 3E is a perspective view of an alternative core wire attachment element according to an embodiment of the present invention.

FIG. 3E illustrates an alternative arrangement depicting a core wire attachment 32'. Rather than having a distal through-hole 38, core wire attachment 32' includes integral boss members 33 on each side that extend perpendicular to, and away from, a central axis of forceps assembly 10. Boss members 33 extend through the constant diameter proximal through-hole 24b of each arm 22, loosely fitting therein without any riveting or welding, thereby connecting the links 22 to attachment 32'. The link arm 22 and the core wire attachment 32' are sized to fit within the small distance between the arms 30 of clevis 20, such that the proximal link arm through-holes 24b remain connected to the boss members 33.

FIGS. 2A-2C illustrate the actuation of the upper and lower jaws 12, 16 between open, partially open, and closed positions, respectively. The elements at the distal end of the forceps assembly 10 are interconnected such that when the core wire 39 distally advances or proximally withdraws core wire attachment 32, jaws 12, 16 pivot between open (FIG. 2A) and closed (FIG. 2C) positions. The forward, distal movement of core wire attachment 32 transfers force through the links 22 to thereby pivot the upper and lower jaws 12, 16 about axle pin 26 to an open position. Conversely, the rearward, proximal movement of core wire attachment 32 transfers force through the links 22 to thereby pivot the upper and lower jaws 12, 16 about axle pin 26 to a closed position.

The connection of axle pin 26, link pins 36, and core wire attachment pin within their respective receiving through-holes can be completed through standard riveting procedures or any suitable alternative connection procedure known to one having ordinary skill in the art. As noted above, where the connection of links 22 to the remaining portion of the forceps assembly is effectuated by a riveting process, the corresponding through-hole may include a raised bevel 23 providing a countersink along the inner surface of the through-hole.

Both the clevis 20 and the jaws 12, 16 may be formed of 416 stainless steel. Alternatively, these components can be manufactured from aluminum, brass, polymeric materials, plastic composites, reinforced ceramics, nitinol, titanium, combined alloys of nickel and titanium, commonly referred to as nitinol, or any other suitable material. Micro precision machining can be used to manufacture these components. Other methods, such as casting, stamping, lithography, metal injection molding, and various deposition techniques known to one having ordinary skill in the art may be used. The jaws 12, 16 can be injection molded and, with secondary processes, coated with nickel plating, gold plating. In addition, through tertiary processes, other coatings such as a thin layer of PTFE (polytetrafluroethelene) or a clear transparent material, such as, for example, parylene may be applied to the jaws. The other components, including the core wire 39, core wire attachment 32, links 22, axle pin 26, and core wire attachment pin (not shown), also can all be manufactured from stainless steel or any other suitable material, such as those described above, and may be made through any suitable process known in the art.

Elongate outer tubular member 50 is connected to and extends proximally from the clevis 20. That connection may be made through any suitable method, including adhesives, soldering, welding, etc. Tubular member 50 may be formed of a flexible, closely wound, stainless steel helical coil and may further include a thin covering or coating, such as a thin layer of PTFE (polytetrafluroethelene) or a clear transparent material, such as, for example, parylene. The flexible coil may be formed to have, for example, a circular, rectangular, or D-shaped cross-section. Other shapes for the cross-section of the coil may be selected depending on the particular application as would be apparent to one having ordinary skill in the art. The coating reduces friction between moving parts, such that the forceps assembly 10 slides more easily within the working channel of a positioning instrument, such as an endoscope. In order to provide a low profile forceps assembly, tubular member 50 may be formed to have, for example, an outer diameter of about 0.0395 inches and a lumen with an inner diameter of about 0.018 inches. These dimensions are exemplary and non-limiting.

FIG. 3D illustrates a fragmentary side view of core wire 39. As noted above, core wire 39 is positioned for relative movement within the elongate member 50 that extends from the actuator 51 to the distal assembly 11. The proximal end of a core wire 39 is inserted into a hypotube (see FIGS. 7 and 8) where it is connected to the spool 56. Spool 56 moves relative to handle 52 for actuation of the core wire 39. At its distal end, the core wire 39 is connected to the proximal end of the core wire attachment 32, through any suitable means, including adhesives, soldering, welding, etc. As seen in FIG. 3D, an intermediate portion 39b of core wire 39, formed between proximal and distal portions 39a, 39c of constant diameter, includes a narrowing taper toward the distal end. Core wire 39 is designed to provide flexibility to the core wire 39, while still retaining torsional stiffness necessary to transmit rotational force to the distal end of the wire 39. Wire 39 can be formed of stainless steel and may also include a thin layer coating (e.g. 0.0001"-0.0007") of PTFE (polytetrafluroethelene) or other suitable material to facilitate its movement within, and lessen the friction force relative to, tubular member 50. In order to provide a low profile forceps assembly, core wire 39 may be formed to have, for example, an outer diameter of about 0.0150 inches along the proximal portion 39a and tapering to a diameter of about 0.0110 inches along a distal portion 39c. As an example, lengths for the core wire portions 39a, 39b, and 39c may be approximately 122.475 inches; 0.250 inches; and 2.875 inches respectively. These dimensions are intended to be exemplary only and may be changed to suit particular applications and access particular treatment regions as would be apparent to one having ordinary skill in the art.

Approximately two inches at both the distal-most and proximal-most ends of the core wire 39 may remain masked during the coating process. The masking leaves these portions uncoated in order to enhance the connection of the core wire distal end to the core wire attachment 32 and the core wire proximal end within the hypotube (see FIGS. 7 and 8).

The right side of FIG. 1 illustrates proximal end components of forceps assembly 10, including actuator 51. As seen in FIG. 1, the elongate outer tubular member 50 extends proximally from the clevis 20 to conned to handle 52 including thumb ring 54. In order to facilitate a wide range of applications and reach targeted anatomical regions of small cross-section, the elongated biopsy forceps device may be formed to a length of between 100 cm and 300 cm, and more preferably between 270 cm and 290 cm. Actuator 51 further includes movable spool 56 capable of being grasped between an operator's index and middle fingers. As noted above, the movable core wire 39 connects at the proximal end of core wire attachment 32, extends proximally within, and is configured to slide relative to, the tubular member 50, and connects to the movable spool 56 in order for the operator to actuate the forceps assembly 10.

Figure 4:
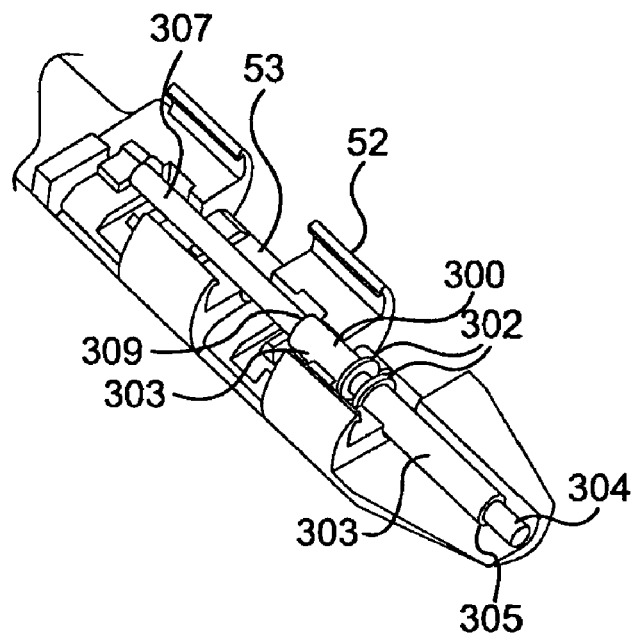
FIG. 4 is a perspective view of a coil retainer within a portion of a handle according to an embodiment of the present invention.
Figure 5:
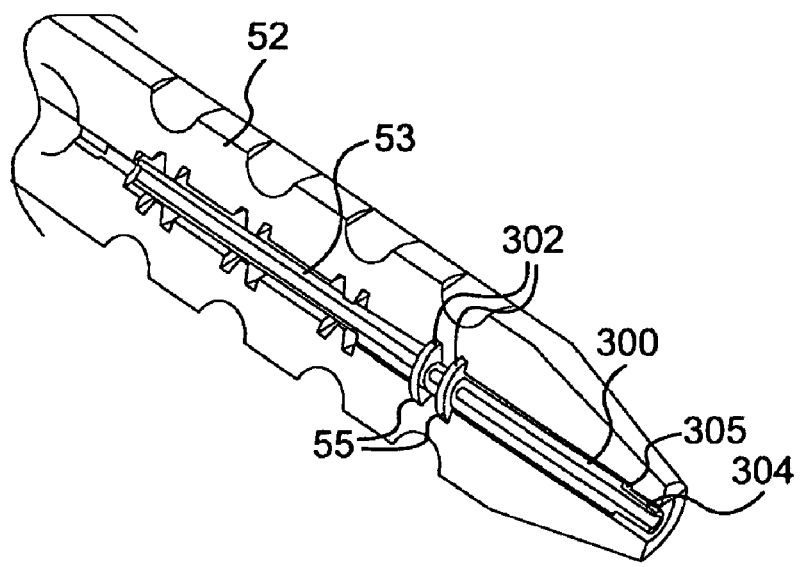
FIG. 5 is a cross-sectional perspective view of the coil retainer of FIG. 4 within a portion of a handle according to an embodiment of the present invention.

FIGS. 4-8 illustrate the components of a handle mechanism for the biopsy device according to an exemplary embodiment of the present invention. FIGS. 4 and 5 illustrate perspective views inside the handle 52 housing a coil retainer 300, according to an embodiment of the present invention. The interior of handle 52 is hollow and defines a lumen 53, which houses the coil retainer 300. Dual fixation flanges 302 prevent any longitudinal movement of the coil retainer 300 within the handle 52. Longitudinal movement of the coil retainer 300 is prevented because flanges 302 are configured to mate with corresponding grooves 55 formed within handle 52 perpendicular to the longitudinal axis of lumen 53.

The proximal end of the tubular member 50 (not shown) will immovably attach within the handle lumen 53 along the exterior of a reduced diameter, stepped down distal portion 304 of the coil retainer 300. A proximal-most face of tubular member 50 extends to abut a distal facing annular flange 305 of retainer 300 resulting from the reduced diameter, stepped down distal portion 304. The coil retainer 300 may be formed of a single integral part and may further include, as most easily seen in FIG. 7, a reduced diameter proximal portion 307. The reduced diameter proximal portion 307 forms a proximal facing annular flange 309 at the point of diameter change. Large diameter portions 303 are formed between the stepped down distal portion 304 and the reduced diameter proximal portion 307. The large diameter portions 303 are sized to match the inner diameter of the handle lumen 53 such that lateral movement of the coil retainer 300 relative to the handle 52 is prevented. The proximal facing annular flange 309 may also assist flanges 302 in preventing longitudinal movement of the coil retainer 300 within the handle lumen 53 by preventing proximal movement of the retainer 300 due to contact between flange 309 and, for example, an internally projecting portion of handle 52.

Figure 7:
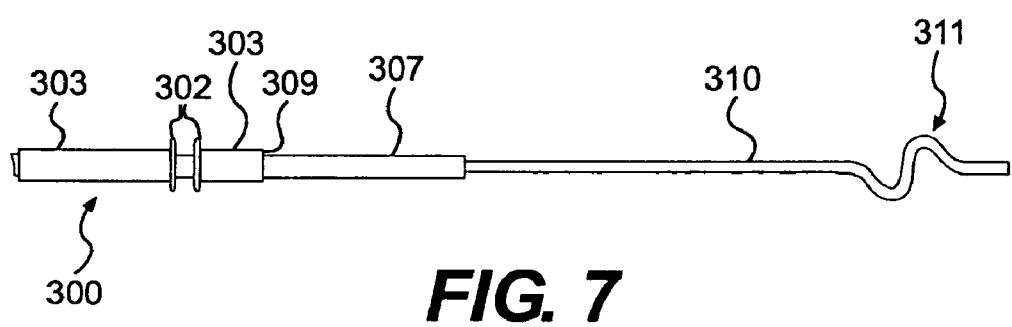
FIG. 7 is a side view of a hypotube and coil retainer assembly according to an embodiment of the present invention.
Figure 8:
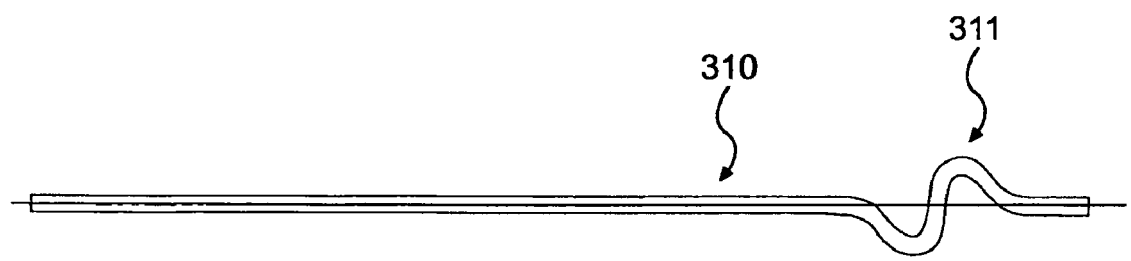
FIG. 8 is a side view of a hypotube according to an embodiment of the present invention.

Referring to FIG. 7, coil retainer 300 is illustrated as housing a hypotube 310 configured to slide within the coil retainer 300. The hypotube 310, in turn, is configured to receive the proximal end of the core wire 39 (FIG. 3D) therein, such that the core wire 39 is secured by a friction fit within an "S" bend 311 and prohibited from movement relative to the hypotube 310. Alternatively, the core wire 39 may be secured to fit within the "S" bend not by means of friction, but simply by means of the curved geometry of the hypotube. This fit, either geometric or friction, provides sufficient coupling of wire 39 to hypotube 310. No other method or means of fixation is necessary to transfer movement of hypotube 310 to wire 39.

The hypotube may be formed of any known polymer materials commonly used in medical devices as would be apparent to one having ordinary skill in the art. Exemplary materials include rigid fluorinated polymers commonly used in medical device applications. The hypotube should be formed of a material capable of receiving the proximal end of core wire 39 in a friction fit and therefore should be selected to have an inner lumen of sufficient size to properly engage core wire 39.

Figure 6:
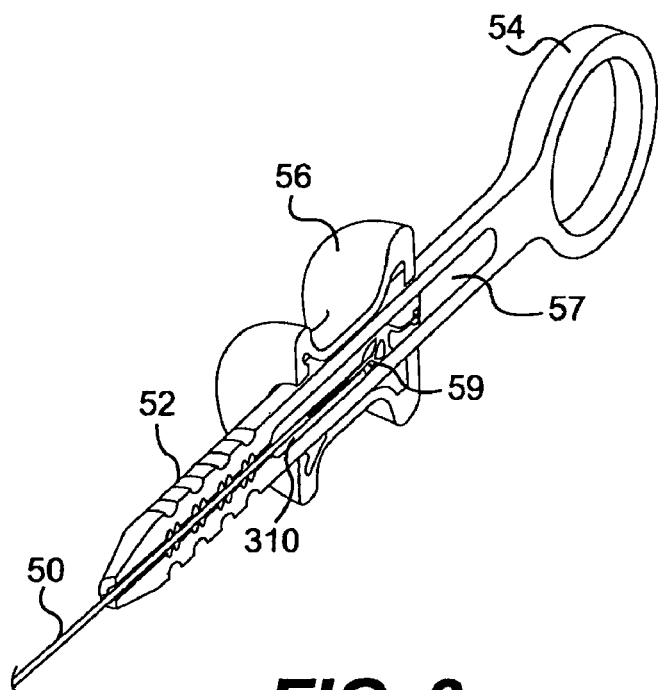
FIG. 6 is a cross-sectional perspective view of a handle, spool, coil, and coil retainer according to an embodiment of the present invention.

As seen in FIG. 6, the handle 52 includes an oval shaped slot 57 that receives hypotube 310 housing the proximal end of the core wire 39. The movable spool 56 includes an exterior surface that slides along the outside of handle 52 and slot 57. The spool 56 also includes an integral portion received within the oval shaped slot 57 of handle 52. That portion includes an "S" channel 59 configured to receive, in a nest, the combined hypotube 310 and core wire 39. As noted above with regard to the hypotube 310, the fit may be secured simply by means of the geometry of the channel 59. In the resulting nest, movement of the spool 56 relative to the handle 52, in turn, moves the core wire 39 within the outer tubular member 50 in order to permit actuation of the forceps assembly. Alternative configurations for the shape of hypotube 310 and channel 59 include, but are not limited to, a circular shape, an "L" shape, and a "Z" shape.

While actuator 51 is described above as a thumb ring and spool arrangement, actuator 51 may be any suitable handle known in the art that controls the movement of an internal core wire for the actuation of a distal forceps assembly.

As seen in FIGS. 2A-2C, each of the upper and lower jaws 12, 16 includes generally outer/convex inner/concave cup-shaped surfaces. Such inner/concave surfaces are designed to retain severed tissue samples therein. The exterior perimeter edge defining a separation portion 40 of the upper jaw 12 is configured to align with a complementary pattern along the exterior perimeter edge defining a separation portion 42 of lower jaw 16 when closed. In FIGS. 2A-2C, both separation portions 40 and 42 of the jaws 12, 16 include lateral, straight edges having one or more teeth 47. The lateral, straight edges of each jaw 12, 16 are connected at their distal ends to a curved, distal edge 44 not including any teeth 47. Each of the teeth 47 projects to form a flat top surface and angled sides.

The teeth 47 of each jaw may form an alternating side tooth configuration. As seen in FIGS. 2A-2C, each jaw includes an arrangement of two teeth 47 on one lateral, straight edge and a single tooth 47 on the opposite, lateral, straight edge. The side tooth configuration of each jaw is arranged such that opposing teeth 47 of jaws 12, 16 are aligned in the closed configuration. The side tooth configuration and alignment provides more separation/retaining surface area to lock the tissue when the jaws are pulled away from the target sampling site after closing on a tissue sample. As seen in FIG. 2C, the complementary side tooth configuration of jaws 12 and 16 results in the formation of a gap 49 at the proximal end of the jaw structure. Due to the alternating arrangement of teeth 47, the gap 49 will extend toward the upper jaw surface on one side (as illustrated in FIG. 2C, for example) and toward the lower jaw surface on the opposite side.

The gap 49 facilitates the complete closure of the forceps jaws at their distal end. The gap 49 facilitates complete jaw closure by accommodating tissue between the proximal ends of the jaws. In addition, the gap prevents the jaws from contacting at their proximal ends. The complete closure of opposing jaw members is particularly advantageous in smaller biopsy devices, where often the small moment arms of the jaws are insufficient to individually separate a clean tissue sample and tissue must often be torn away from the treatment site upon pulling the closed forceps backward. Alternative designs of a gap formed by a taper from the proximal end to the distal end will serve the same purpose.

The upper jaw 12 in FIGS. 2A-2C is comprised of a biopsy cutter containing at least one fenestration hole 58 in the center of the jaw, while the lower jaw 16 includes at least one spike feature to aid in retaining tissue. The fenestration hole 58 allows for fluids and/or air to escape the jaws during tissue retrieval and thereby aids in the volume of tissue acquisition between the jaws. The fenestration hole 58 can be used as a specimen flushing port to remove a captured sample from between the jaws once the forceps assembly is removed from the treatment site.

The spike feature aids in retaining tissue captured within the forceps when the forceps device is pulled away from the targeted site after pivoting to capture a sample. A pyramid-shaped spike 62 is formed within the lower jaw 16 having a pointed tip 67 extending towards the fenestration hole 58 of the upper jaw 12. The tip of the pyramid-shaped spike 62 may terminate to form a small flat square shape or, alternatively, may be formed to terminate at a sharp spike. The pyramid-shaped spike 62 will penetrate the tissue at the target site and the forceps device can not be pulled free until some tissue breaks loose. Such tissue retention features are particularly advantageous in separating and capturing tissue samples in anatomical regions having relatively small cross-section areas, where often the small moment arms of the jaws are insufficient to separate a tissue sample.

The spike feature and fenestration hole of the jaws work together to facilitate the capture of tissue samples. The pyramid-shaped spike 62 can be positioned to align with the fenestration hole 58 such that the tip 67 of the spike 62 is pointed towards the fenestration hole 58 when the jaws are in the closed position. The pyramid-shaped spike 62 does not protrude through the fenestration hole 58 but may terminate at or below the base of the fenestration hole 58. Such an arrangement secures tissue between the protruding pyramid-shaped spike 62 and the inner surface defining the fenestration hole 58. The size of the pyramid-shaped spike 62 can be varied depending on the need to grasp and retain tissue and depending on the particular tissue targeted and the sample size desired.

The lower jaw 16 may contain more that one pyramid-shaped spike 62 to aid in the retention of tissue. Similarly, the upper jaw 12 may include more than one fenestration hole 58 aligned with each pyramid-shaped spike 62 or, alternatively, offset from a pattern of spikes. The lower jaw 16 can be machined so as to form the pyramid-shaped spike 62 integral with the lower jaw surface. The pyramid spike 62 can be machined to exhibit four orthogonal surfaces or faces 63A-63D forming triangles that meet at a common sharp spike point 67. The faces 63A-63D each may be substantially concave. The orthogonal faces can be machined such that adjoining faces meet with each other to form a distinct pronounced edge. Faces 63B and 63C, for example, meet to form a distinct edge between the base of the pyramid-shaped spike 62 and the sharpened tip point 67.

The cavities around the pyramid spike 62 can be machined out using a small ball end mill such that distinct concave surfaces 63A-63D are formed on the distal, proximal, and lateral sides of the pyramid spike 62. The separate concave surfaces 63A-63D provide the advantage of further tissue retention by allowing target tissue penetrated by the pyramid spike 62 to rest below the base of the pyramid spike 62 during a biopsy procedure. Upon penetration by the pyramid spike 62, captured tissue can be securely trapped between the concave surfaces, formed around the pyramid spike 62 on one side, and the fenestration hole 58 as well as the inner/concave surface of the upper jaw on the other side. The four surfaces 63A-63D, provide an additional advantage of friction and resistance against captured tissue as the device is pulled away from target tissue. The orthogonal shape provides better retention in that captured tissue may slide off a spike having a smooth outer surface.

Figure 9A:
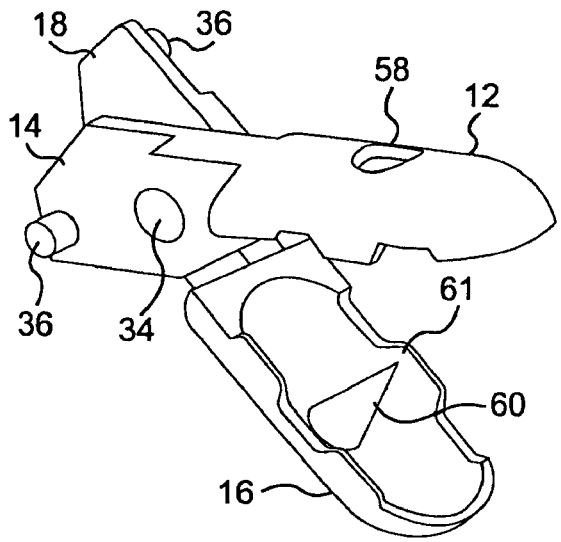
FIG. 9A is a perspective view of a side tooth forceps jaw assembly having a conical spike in the lower jaw according to an embodiment of the present invention.
Figure 9B:
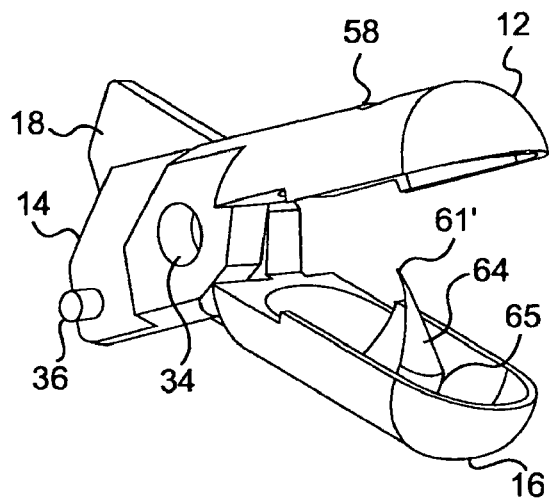
FIG. 9B is a perspective view of forceps jaw assembly having an alternative spike arrangement in the lower jaw according to an embodiment of the present invention.

FIGS. 9A and 9B depict particular forceps jaw designs according to an embodiment of the invention. The jaws shown in FIGS. 9A and 9B are substantially the same as jaws shown and described with reference to FIGS. 2A-2C, except as discussed herein. The same reference numerals have been used for the same or substantially similar parts of the jaws. Like the embodiment of FIGS. 2A-2C, each lower jaw 16 shown in FIGS. 9A and 9B includes at least one spike feature to facilitate retaining tissue captured within the forceps when the forceps device is pulled away from the targeted site after pivoting to capture a sample. The FIG. 9A embodiment includes a sharp conical spike 60 having a sharp tip 61 extending to a fenestration hole 58 of an upper jaw 12. The conical spike 60 of jaw 16 is pointed towards the fenestration hole 58 when the jaws are in the closed position. The size of the conical spike can be varied, depending on the need to grasp and retain tissue, and depending on the particular tissue targeted and sample size desired. Unlike the embodiment including pyramid-shaped spike 62, lower jaw 16 including conical spike 60 does not include distinct and separate concave surfaces 63A-63D formed around the base of conical spike 60. Instead, the inner surface of jaw 16 is continuous, substantially concave, and cup-shaped outside of the portion occupied by conical spike 60.

The embodiment of FIG. 9B includes a sharp proximally curved spike 64 having a sharp tip 61' and extending from the inner concave surface of lower jaw 16. The proximally curved spike 64 is integrally formed with a spike base 65. The proximally curved spike 64 and spike base 65 are configured to "push" or "squeeze" the tissue towards the proximal end of the jaw during closing action. The resulting forces applied to the captured tissue prevent the tissue from slipping out of the jaws while the biopsy device is pulled away from the target site. Just as in the embodiment of FIG. 9A, the spike 64 may be pointed towards the fenestration hole 58 when the jaws are in the closed position. Due to the proximally curved shape of spike 64, the tissue fenestration hole 58 on the opposite jaw may be offset toward the proximal end of the jaw in order to complement the proximally directed forces acted upon tissue. The proximally curved spike 64 is particularly useful in piercing and retaining tissue when the forceps jaws are closed and the forceps assembly is proximally pulled away from target tissue. In the manner of a snake's fangs, the spike 64 will provided added friction and resistance against captured tissue as the device is pulled away from target tissue.

Figure 9C:
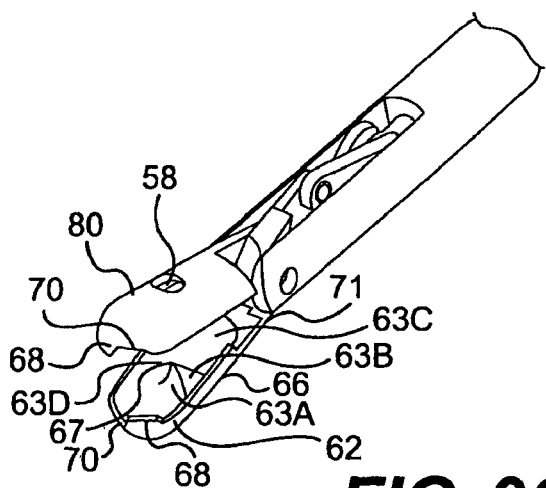
FIG. 9C is a perspective view of a front tooth forceps jaw assembly having a spike in the lower jaw according to an embodiment of the present invention.

Referring to FIG. 9C, a lower jaw 66 is depicted including multiple distinct concave surfaces 63A-63D formed around a pyramid-shaped spike 62 having a spike point 67. The cutting perimeter of jaw 66 includes a single curved tooth 68 positioned next to a recess 70 along the distal curved portion of the cutting perimeter. As seen in FIGS. 9C, 10A, and 10E, the tooth 68 is offset from a center of the distal curved portion and projects to form a flat top surface and angled sides along the distal curved portion. The recess 70 forms a shape complementary to the tooth 68, exhibiting a flat base and angled sides. The tooth and recess pattern of jaw 66 will be matched by an opposing tooth and recess pattern of an upper jaw to provide a closed surface between the jaws during use. For example, FIGS. 9C and 10E illustrate an upper jaw 80 having a fenestration hole 58 opposed to the pyramid-shaped spike 62 of lower jaw 66. In addition upper jaw 80 includes a tooth and recess pattern matching and complementing the tooth and recess pattern of lower jaw 66 in FIGS. 9C and 10A. FIG. 9C depicts the complementary configuration of jaws 66 and 80 in FIGS. 10A and 10E formed in a forceps assembly and illustrated in a position between the fully opened and fully closed position.

FIGS. 9C, 10A, and 10E illustrate an additional feature of a stepped-down heel portion 71 at the proximal end of the inner/concave substantially hemispherical cup shaped jaw surface. Stepped-down heel portions 71 facilitate the complete closure of the forceps jaws at their distal end. The stepped-down heel portion is designed to facilitate complete jaw closure even when tissue may be present between the proximal-most portions of opposing jaw members. As the jaws close around a targeted tissue portion, the distal end surfaces of the jaws are not prevented from closing due to tissue positioned at the proximal-most portions of opposing jaw members. Complementary stepped-down heel portions 71 of opposing jaw members form a distinct gap at the proximal end of the closed jaw members for accommodating such tissue that would otherwise inhibit jaw closure. The complete closure of opposing jaw members is particularly advantageous in smaller biopsy devices, where often the small moment arms of the jaws are insufficient to separate a tissue sample and tissue must often be torn away from the treatment site upon pulling the closed forceps proximally.

It is to be understood that the spike and fenestration hole can be arranged on either the upper or lower jaw, and in alternative arrangements the jaws may include multiple spikes and fenestration holes.

FIGS. 10A-10E depict various cutting patterns formed along the cup shaped perimeter of forceps jaws according to other exemplary embodiments of the present invention. Irrespective of whether each jaw depicted in FIGS. 10A-10E is designated as an "upper jaw" or "lower jaw," it is to be understood that the cutting patterns of opposing jaws are configured to align with and exhibit a pattern complementary to one another. The jaws are intended to complement each other such that the edges align without any substantial space therebetween when closed.

As noted above, FIG. 10A depicts a lower jaw 66 including multiple distinct concave surfaces 63A-63D formed around a pyramid-shaped spike 62 having a spike point 67. The cutting perimeter of jaw 66 includes a single curved tooth 68 positioned next to a recess 70 along the distal curved portion of the cutting perimeter.

FIG. 10B illustrates an upper jaw 72 having a standard uniform separation perimeter and a fenestration hole 58. Jaw 72 exhibits a "U" shaped separation perimeter 69. The separation perimeter 69 does not include any teeth as in previous examples and can be machined to have a particular sharpness, depending on the particular tissue targeted. Again, a stepped-down heel portion 71 is provided to permit distal edge contact of the upper and lower jaws so the tissue will not slip out upon proximal movement of the forceps device.

Referring to FIG. 10C, an upper jaw 74 is illustrated depicting a oval-shaped sharpened separation perimeter edge 76 useful for cutting soft tissue. The jaw 74 includes an inner concave jaw surface 77 including a fenestration hole 58. A terminal portion 79 of the inner jaw surface can be machined to exhibit a thinner wall portion leading to the cutting edge 76.

FIG. 10D illustrates upper jaw 12 of FIGS. 2A-2C, showing the inside surface of jaw 12 and the alternating side tooth cutting pattern. The cutting patterns of the various jaws shown and described herein, including the jaws of FIGS. 10A-10E, are designed to provide more separation/retaining surface area to lock the tissue when the jaws are pulled away from the target sampling site.

Figure 11A:
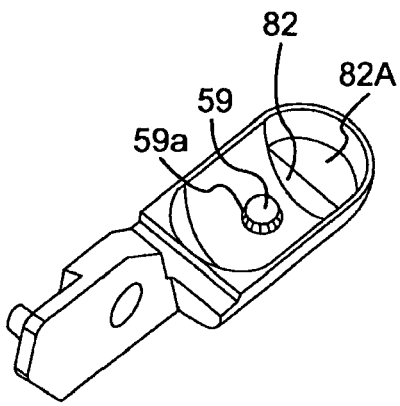
FIGS. 11A-11E illustrate various internal tissue retention features for the forceps jaws according to embodiments of the present invention.

FIGS. 11A-11D depict various internal tissue retention features for the forceps jaws according to embodiments of the present invention. FIGS. 11A-11D illustrate structural features within the inner/concave cup shaped jaw surfaces designed to add retention force to separate and retain tissue while the biopsy device is pulled away from the target site. FIG. 11A, for example, depicts a jaw including a step feature 82 occupying a distal portion of the inner/concave substantially hemispherical cup shaped jaw surface. An opposing jaw may include the same or a similar feature. When upper and lower jaws having the configuration of FIG. 11A come together, the raised, horizontal flat surfaces 82a of the step features 82 present a smaller space or volume between the jaws and thus higher compression force is exerted on the captured tissue. The sharp transition from the inner/concave cup shaped jaw surface to the upper flat surface 82a of the step feature 82 would also provide higher resistance to prevent tissue from slipping out of the jaws.

In addition, FIG. 11A depicts an alternative fenestration hole 59, formed to provide an additional tissue retention function. For example, the edge of the jaw surface defining the fenestration hole 59 can be raised above the remaining inner concave cup shaped surface. The edge may be raised to form a generally frusto-conical, volcano shaped projection 59a. The raised projecting portions along the edge of the fenestration hole 59 can serve to project into a captured tissue sample, thereby more forcefully retaining the sample upon proximal movement of the forceps assembly. Features such as the slope and height of frusto-conical shaped projection 59a can be altered depending on factors such as, for example, the particular procedure and tissue type being captured. The volcano shaped projection 59a provides the combined benefits of a fenestration hole and a tissue retention feature. The jaws of the forceps assembly may include the alternative fenestration hole 59 either alone, or in addition to, other tissue retention features as described herein.

Figure 11B:
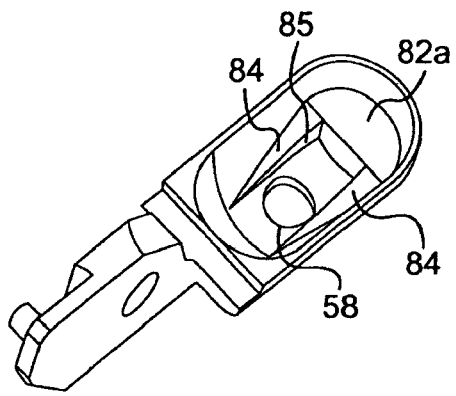

FIG. 11B depicts a jaw having a step feature 82 similar to FIG. 11A and further including wedges or ramps 84, configured to "push" or "squeeze" the tissue towards the proximal end of the jaw during closing action. The resulting forces applied to the captured tissue prevent the tissue from slipping out of the jaws while the biopsy device is pulled away from the target site. As seen in FIG. 11B, the jaw includes dual triangular ramps 84 that incline upwardly toward a distal end of the jaw. Ramps 84 incline and terminate at the upper flat surface 82a of the step feature 82. Ramps 84 may be positioned on opposing sides of a fenestration hole 58 formed in the inner concave cup surface of the jaw. In addition, the ramps 84 may be formed to exhibit inner side faces 85 orthogonal to the upper surfaces of ramps 84 within the inner jaw surface. The resulting configuration of FIG. 11B provides the combined benefits of tissue retention provided by step feature 82 and ramps 84. It is contemplated that the ramp may assume configurations other than that depicted in FIG. 11B.

Figure 11C:
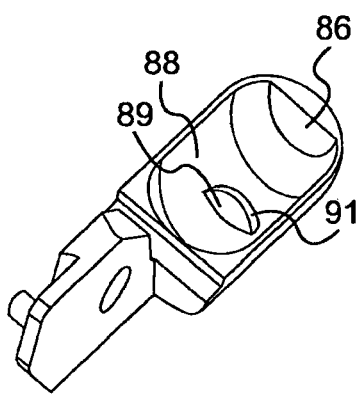

FIG. 11C depicts a jaw having a flat proximally directed face 86 at the distal end of the inner/concave cup shaped jaw surface and a protrusion 88 at a center of the jaw. The protrusion 88 may include a flat proximal surface 89 and a rounded surface 91, distally projecting from the proximally directed surface 89. The vertical drop presented by the face 86 provides higher resistance to captured tissue movement than a curved inner surface. In addition, the raised protrusion 88 projects against captured tissue and provides additional resistance to the movement of captured tissue within the inner jaw surface.

Figure 11E:
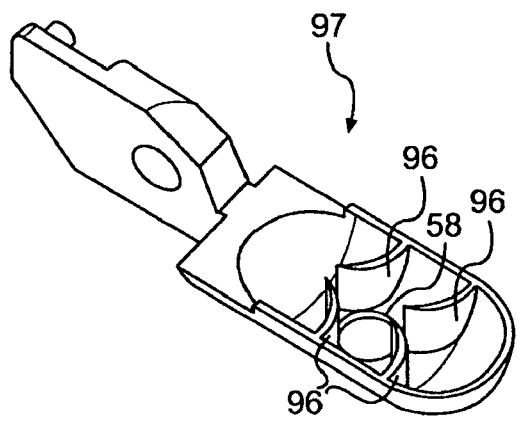
Figure 11D:
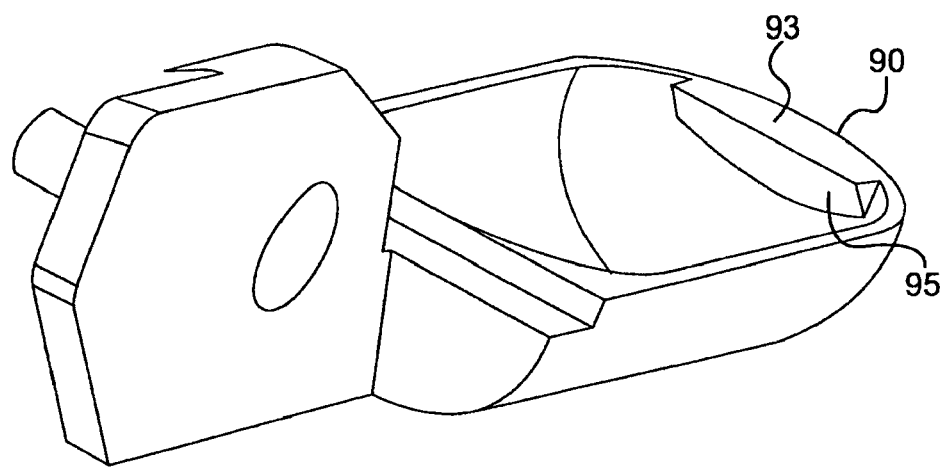

FIG. 11D depicts a jaw with an inclined, proximally directed lip 90 formed at the distal end of the inner/concave cup shaped jaw surface. Lip 90 includes a flat upper surface 93 that meets with a portion of the curved distal perimeter at the upper edge of the jaw. The flat upper surface 93 of lip 90 meets at its proximal end with an inclined face 95 that extends distally to meet a portion of the inner concave surface of the jaw. Lip 90 is configured to "push" or "squeeze" the tissue towards the proximal end of the jaw during closing action. In addition, lip 90 is configured to provide higher resistance and "hold" the tissue when the forceps assembly is pulled away from tissue. The resulting forces applied to the captured tissue through the lip 90 both hold the tissue and aid in preventing the tissue from slipping out of the jaws while the biopsy device is pulled away from the target site.

FIG. 11E depicts a jaw 97 with multiple curved fins 96 proximally directed and formed at the inner/concave cup shaped jaw surface. Curved fins 96 serve to capture and retain tissue between the fins 96 during closing action. The fins 96 will provide greater retention capability by both directing the tissue proximally within the inner jaw surface as well as projecting against captured tissue to provide additional resistance to the movement of captured tissue within the inner jaw surface. The top of the fins 96 can extend to a height such that the fins 96 are flush with the surface defined by the outer separation perimeter of jaw 97. The fins 96 may be arranged in rows along the inner concave surface of the jaw 97 and on opposite sides of a fenestration hole 58. Alternatively, the fins 96 may be formed in a non-symmetrical alternating arrangement. Additional features, such as the number of fins 96, the extent the fins 96 are curved, and the thickness of the fins 96, can be altered depending on the particular application.

In addition to the tissue retention features described above, the surface finish of the jaws may be configured to improve tissue retention. For example, the inner surface of the jaws may be roughened through any suitable method to more frictionally engage tissue. A Ra range between 50 to 250 could be considered for the internal surface of the jaws in order to enhance tissue retention.

Figure 12A:
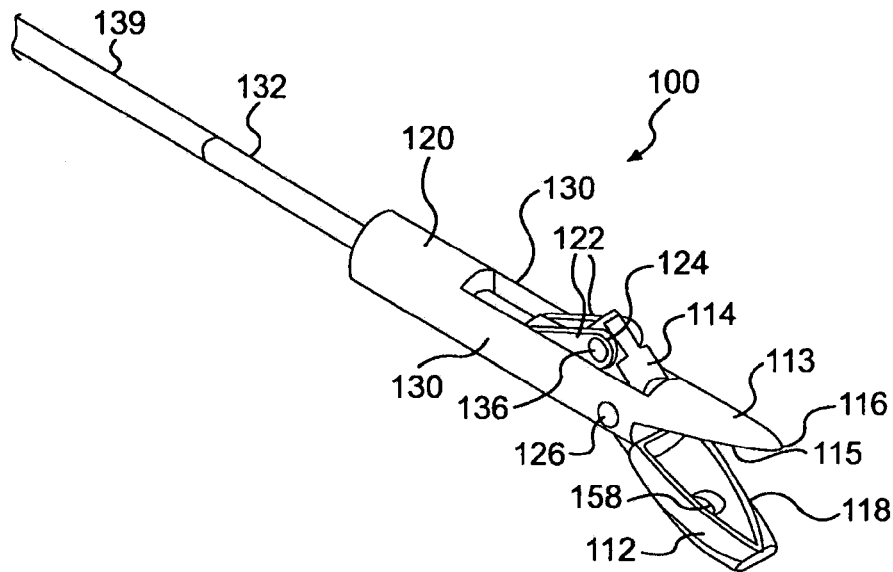
FIGS. 12A-12C illustrate components of a knife jaw biopsy assembly according to an embodiment of the present invention.
Figure 12B:
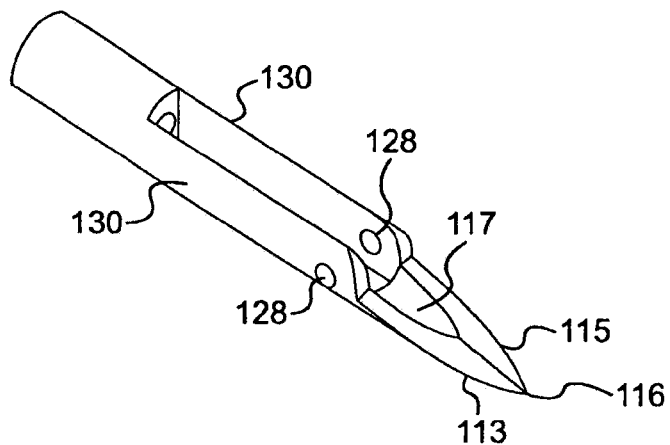
Figure 12C:
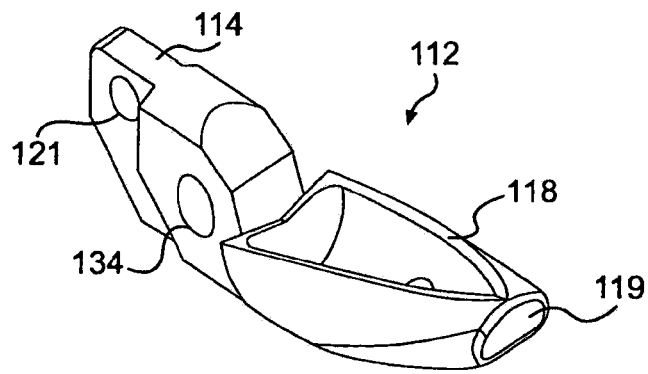

Referring to FIGS. 12A-12C, a biopsy device 100 including a movable jaw 112 is illustrated. The biopsy device 100 further comprises a clevis 120 having a fixed jaw comprised of an integrated knife blade 113. An upper profile of the movable jaw 112 matches the profile of the fixed jaw's blade surface. The main components at the distal end of the biopsy device 100 include movable jaw 112 having a unitary proximal tang 114, a pair of link arms 122 having link arm through-holes 124 at their proximal and distal ends, and the clevis 120. The distal end of clevis 120 includes opposing pivot arms 130 with an axle pin 126 running between axle holes 128 on opposing pivot arms 130 of the clevis 120. The center of the clevis 120 is hollow and configured to receive the distal end of a core wire attachment 132 that extends proximally to a core wire 139, which itself connects to a handle actuation mechanism.

Other than including the feature of an integral fixed jaw comprised of a knife blade 113, the clevis 120 is similar to the clevis 20 described above. The fixed jaw comprised of knife blade 113 includes a generally convex outer surface and an outer perimeter defining edges 115 that extend distally to meet at a sharpened point 116. Edges 115 may be sharpened to further aid in the penetration of tissue. As seen in FIG. 12B, the inner surface of knife blade 113 may include an arch shaped concave indentation 117 to aid in tissue retention during penetration.

The perimeter defined by edges 115 complements the outer separation perimeter 118 of the movable jaw 112 such that the edges align without any substantial space therebetween when movable jaw 112 is closed. The outer separation perimeter 118 of the movable jaw 112 may define a substantially-triangular shape, for example. The jaw 112 may also include a flat distally directed surface 119 at the front end of the jaw and an inner concave surface for capturing severed tissue samples. The movable jaw 112 further includes a mounting bore 134 for receiving the axle pin 126, which also runs through the axle holes 128 on opposing pivot arms 130 of the clevis 120. The proximal tang 114 of jaw 112 includes a link pin bore 121 for receiving a link pin 136, which also runs through the link arm through-holes 124 at the distal end of both link arms 122. Just as in the previously described embodiments, the link arm through-holes 124 at the proximal end of both link arms 122 connect via a pin to the core wire attachment 132. The jaw 112 thereby pivots relative to the clevis 120 and the knife blade 113 upon distal or proximal movement of the core wire attachment 132. In addition, jaw 112 can also include a fenestration hole 158 within the inner/concave cup shaped jaw surface.

Compared to conventional biopsy forceps where two movable jaws open at the same time, this biopsy device 100 allows biopsies to be taken in a smaller ductile system and can penetrate deeper into the tissue and obtain a sample of greater depth. Greater depth is achieved because the opening of this device is only half that of the pinch biopsy forceps having two movable jaws. The knife blade 113 can be used to penetrate deeper into the target site and the moving jaw 112 will close on a bigger and deeper sample for histological evaluation. The biopsy device 100 would be particularly beneficial in cases where the target site is closely attached to the ductile wall and a tangential sample is desired. The knife blade 113 can be used to access the tissue sample along the axis of the working channel of an endoscope, for example, at which point the movable jaw 112 can be actuated to close upon the opposing tissue surface to sever the sample.

Figure 13A:
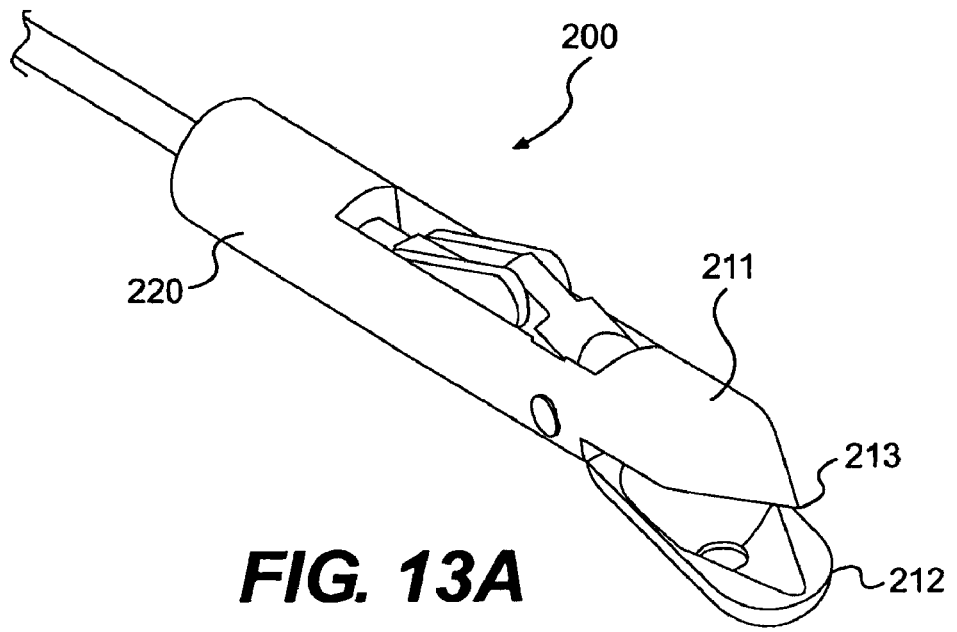
FIGS. 13A-13C illustrate components of a needle jaw biopsy assembly according to an embodiment of the present invention.
Figure 13B:
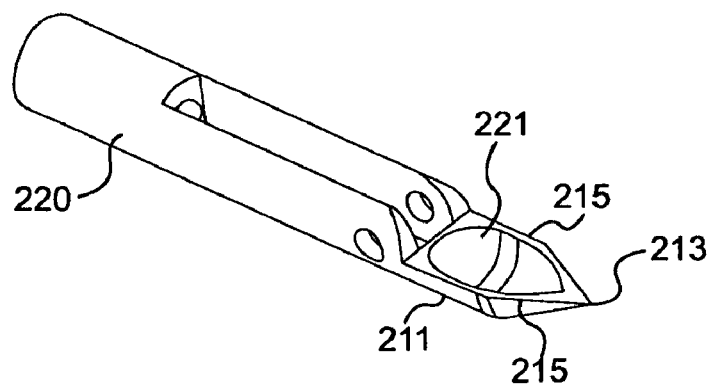
Figure 13C:
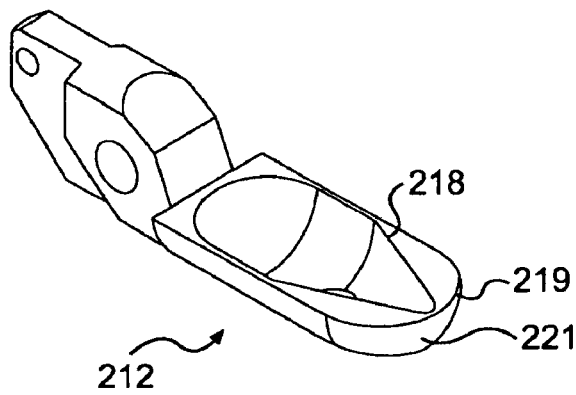

Referring to FIG. 13A-13C, a biopsy device 200 including a movable jaw 212 is illustrated. The biopsy device 200 further comprises a clevis 220 having a fixed jaw comprised of an integrated projection 211 that narrows to a tissue penetrating needle tip 213. As seen in FIG. 13B, the actuation components of the biopsy device 200, including the link arms, core wire attachment, core wire, and various pins, are similar to those described in FIGS. 12A-12C above and therefore their description has not been repeated.

The integrated projection 211 of clevis 220 includes a concave inner surface 221 along the inner side of the integrated projection 211. The inner concave surface 221 aids in the retention of tissue after the needle tip 213 penetrates targeted tissue. The projection 211 includes a generally convex outer surface and a perimeter along the inner side of the projection defining edges 215 that extend distally to meet at the sharpened needle tip 213. Edges 215 may be sharpened to further aid in the penetration of tissue.

The perimeter defined by edges 215 complements the inner separation perimeter 218 of the movable jaw 212 such that the edges align without any substantial space therebetween when movable jaw 212 is closed. The distal portion of inner separation perimeter 218 narrows to a distal point 219 that is aligned with the needle tip 213 when the movable jaw 212 is closed. The jaw 212 may also include a rounded distally directed surface 221 at the front end of the jaw in order to facilitation the introduction of the biopsy device 200 within a placement instrument, such as the working channel of an endoscope.

The biopsy device 200 includes many advantages similar to the biopsy device 100 described above, such as, for example, operating in small ductile system and deeper penetration into the tissue. In addition, the device 200 could be used to sample particularly rigid cancer tissue in the bile duct. The penetrating needle tip 213 is capable of penetrating a relatively hard mass and acquiring tissue samples therefrom.

Figure 14:
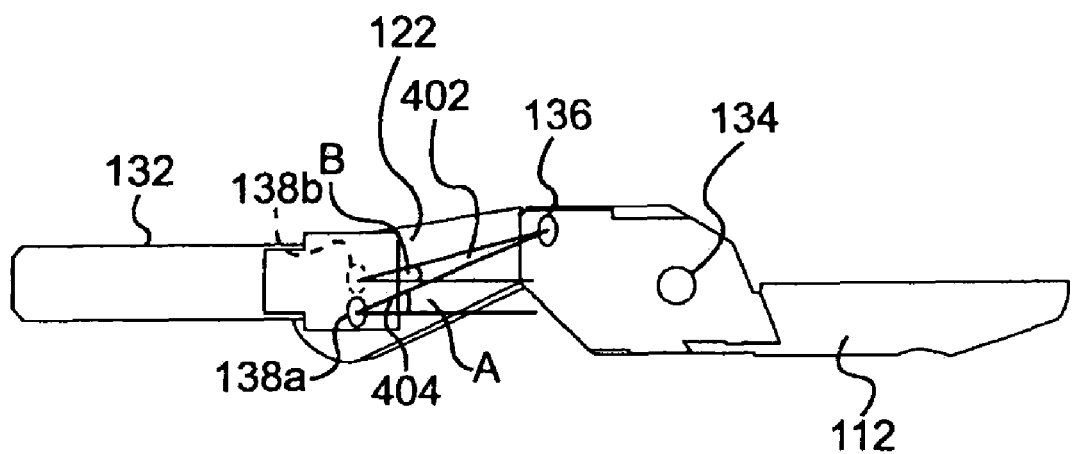
FIG. 14 is a side view of the moving components for a single jaw biopsy assembly according to an embodiment of the present invention.

FIG. 14 illustrates an additional advantage of the single movable jaw biopsy devices described in FIGS. 12A-13C. FIG. 14 depicts a side view illustrating the linked components of a jaw 112 with an integral link pin 136 and a mounting bore 134, a link arm 122, and a core wire attachment 132 having a pivot hole 138a. Because of the single movable jaw design in the FIGS. 12A-13C, the pivot hole 138a (shown in solid lines) on the core wire attachment 132 could be located asymmetrically (i.e. shifted toward the bottom of FIG. 14). Because the proximal link arm through-hole 124 remains in the same position (at pin 36 shown in FIG. 14), the displacement of core wire attachment 132 provides more room (within the available area inside the inner lumen of the clevis) for the link arm 122 to achieve a greater resting angle A relative to the bottom surface of FIG. 14.

FIG. 14 depicts a line 402 connecting the center of link pin 136 and a pivot hole 138b, represented by a dashed circle, as positioned in embodiments with two movable jaws. Line 404 illustrates a line connecting the center of pivot pin 136 and the center of asymmetrically located pivot hole 138a in the embodiments of FIGS. 12A-13C. As is geometrically evident, line 404 forms an angle A relative to the horizontal, and line 402 forms an angle B relative to the horizontal, wherein angle A is greater than angle B. The greater resting angle A, in turn, allows for a greater moment to be generated about the mounting bore 134 of jaw 112 than can be generated in a dual jaw configuration.

Figure 15A:
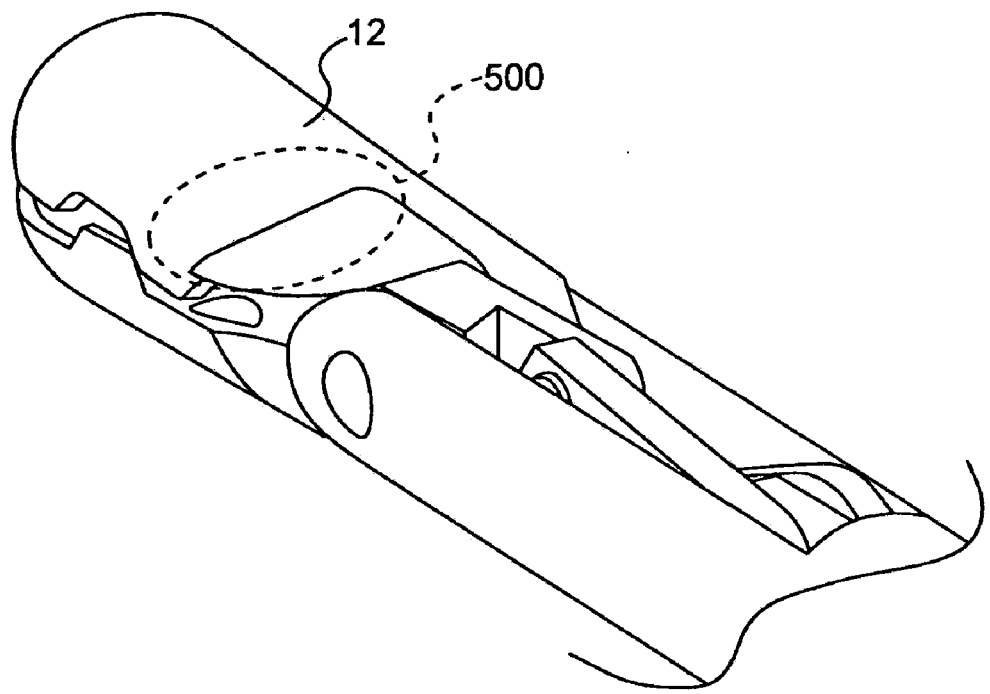
FIGS. 15A and 15B are perspective views of a forceps assembly, illustrating rounded features of the assembly, according to an embodiment of the present invention.
Figure 15B:
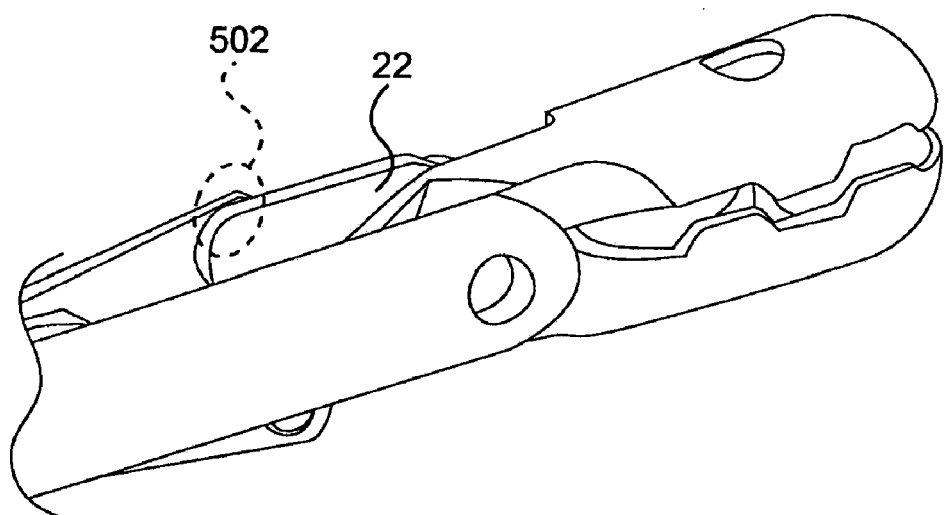

FIGS. 15A and 15B are perspective views, from the proximal side of the distal assembly 11 shown and described in FIGS. 2A-2C. FIGS. 15A and 15B illustrate additional features and advantages of embodiments of the invention. Due to the small profile intended for the forceps device (e.g. approximately 0.5-2 mm outer diameter), and the constraints of certain small working channels within endoscopes (e.g. as small as 1.2 mm inner diameter), the outer surfaces of the forceps assembly can be coated with a thin layer of lubricious material to ease introduction and removal of the small profile device within a scope channel. In addition, components of the forceps device can be machined to exhibit rounded smoothed surfaces, such as those illustrated in FIGS. 15A and 15B to further facilitate movement of the assembly within a small profile scope channel. For example, FIG. 15A illustrates a rounded portion 500 of the outer convex proximal portion of upper jaw 12. FIG. 15B, for example, illustrates a proximal end of a link 22 rounded to exhibit a curved atraumatic smooth surface 502. Various other surfaces may be rounded, chamfered, and/or tapered. These surface features facilitate withdrawal of the device from an endoscope channel.

The forceps devices according to embodiments of the present invention may also be configured so as to conduct electrosurgical energy to the patient's tissues in order to cauterize the treated tissue region during and/or after sample collection. Accordingly, the forceps jaws may be connected to a source of high frequency current conducted through the jaws at the distal assembly 11. The energy may be provided in monopolar or bipolar form at the distal assembly 11. For example, bipolar electrosurgical energy may be provided at the distal end of the jaw assembly such that one jaw acts as an active electrode with the opposing jaw acting as the return electrode in a bipolar circuit through tissue. Alternatively, one or both jaws could be connected to a monopolar source of energy, such that the combined jaws act as an active electrode and an electric circuit is completed with an external return electrode pad attached at some point along a patient's external skin surface. If conductive, the forceps assembly 11 may be electrically connected to a suitable power source known in the art (e.g., RF generator) via suitable electrical connections known in the art (e.g., electrical leads and/or wires or through member 50 and/or wire 39). The power source may be disposed anywhere on or relative to the device 10, for example, at the handle 52 or connected to the handle 52.

The aforementioned embodiments may be used in any medical or non-medical procedure, including any medical procedure where a tissue sample is desired from any body lumen. In addition, at least certain aspects of the aforementioned embodiments may be combined with other aspects of the embodiments, or removed, without departing from the scope of the invention. For example, any of the tissue retention features of FIGS. 11A-11E may be included in the configuration of FIGS. 12A-13C or any other jaw configuration disclosed herein. In addition any of the jaw features described with regard to FIGS. 10A-10E, for example, also may be included in the configuration of FIGS. 12A-13C or any other jaw configuration disclosed herein.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:
   a proximal actuator;
   a clevis; and
   a distal assembly including:
     a fixed jaw integrally formed with the clevis, the fixed jaw including a first outer perimeter defining a first cutting edge; and
     a movable jaw coupled to the clevis and pivotable relative to the fixed jaw by actuation of the proximal actuator, the movable jaw including a cup having an opening, wherein the opening includes a second outer perimeter, and wherein side edges of the opening extend from a proximal end of the opening to a distal end of the opening and meet at a sharp distal point of the opening;
     wherein the second outer perimeter of the movable jaw complements the first outer perimeter of the fixed jaw.

2. The medical device of claim 1, wherein a shape of the second outer perimeter is the same as a shape of the first outer perimeter.

3. The medical device of claim 1, wherein the first cutting edge of the fixed jaw includes a sharp distal point.

4. The medical device of claim 1, wherein the second outer perimeter defines a second cutting edge, and wherein, when the movable jaw is closed, the second cutting edge of the movable jaw and the first cutting edge of the fixed jaw align without space between the first and second cutting edges.

5. The medical device of claim 1, wherein the fixed jaw includes a concave inner surface.

6. The medical device of claim 1, wherein an inner surface of the fixed jaw includes an arch-shaped concave indentation.

7. The medical device of claim 2, wherein the shape of the second outer perimeter of the movable jaw is a triangular shape.

8. The medical device of claim 2, wherein the shape of the second outer perimeter of the movable jaw is a teardrop shape.

9. The medical device of claim 1, wherein the cup of the movable jaw includes an inner concave surface for retaining a severed tissue sample.

10. The medical device of claim 1, wherein the clevis includes a pivot hole about which the movable jaw pivots upon actuation of the proximal actuator.

11. The medical device of claim 10, further comprising an elongate member connecting the proximal actuator to the distal assembly.

12. The medical device of claim 11, further comprising a wire extending though the elongate member for coupling the movable jaw to the proximal actuator, and wherein the movable jaw connects to the wire by a pair of links.

13. The medical device of claim 1, wherein the fixed jaw includes a projection that narrows to a tissue penetrating needle tip.

14. The medical device of claim 13, wherein the projection includes a concave inner surface.

15. A medical device, comprising:
   a proximal actuator;
   a clevis; and a distal assembly including:
- a fixed jaw integrally formed with the clevis, the fixed jaw including a pointed distal end and a first outer perimeter defining a first cutting edge; and
- a movable jaw coupled to the clevis and pivotable relative to the fixed jaw by actuation of the proximal actuator, the movable jaw including a non-pointed distal end and a cup having an opening, wherein the cup includes a second outer perimeter, and wherein side edges of the opening extend from a proximal end of the opening to a distal end of the opening and meet at a sharp distal point of the opening;
- wherein the second outer perimeter of the movable jaw complements the first outer perimeter of the fixed jaw.

16. The medical device of claim 15, wherein the first cutting edge of the fixed jaw includes the pointed distal end.

17. The medical device of claim 15, wherein the non-pointed distal end of the movable jaw includes a rounded, distally directed surface.

18. The medical device of claim 15, wherein the non-pointed distal end of the movable jaw includes a flat, distally directed surface.

19. A medical device, comprising:
a proximal actuator;
a clevis; and
a distal assembly including:
- a fixed jaw integrally formed with the clevis, the fixed jaw including a pointed distal end and a first outer perimeter defining a first cutting edge; and
- a movable jaw coupled to the clevis and pivotable relative to the fixed jaw by actuation of the proximal actuator, the movable jaw including a non-pointed distal end and a cup having an opening, wherein the opening includes a second outer perimeter, wherein side edges of the opening extend from a proximal end of the opening to a distal end of the opening and meet at a sharp distal point of the opening, wherein the opening narrows from the proximal end to the distal end, wherein the sharp distal point of the opening is proximal to the non-pointed distal end of the movable jaw;
- wherein the second outer perimeter of the movable jaw complements the first outer perimeter of the fixed jaw, and wherein the sharp distal point of the movable jaw is aligned with the pointed distal end of the fixed jaw when the movable jaw is closed.

20. The medical device of claim 19, wherein the non-pointed distal end of the movable jaw includes a rounded, distally directed surface.

* * * * *